US012595459B2

(12) United States Patent
Jaffray et al.

(10) Patent No.: US 12,595,459 B2
(45) Date of Patent: Apr. 7, 2026

(54) DEVICE, SYSTEM AND PROCESS FOR ROBOTIC RADIOBIOLOGY

(71) Applicant: UNIVERSITY HEALTH NETWORK, Toronto (CA)

(72) Inventors: David A. Jaffray, Etobicoke (CA); Bradly G. Wouters, Toronto (CA); Alexander Ralph Lino Jaffray, Etobicoke (CA); Ryan Steven Elliott, Cobourg (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 843 days.

(21) Appl. No.: 15/999,534

(22) PCT Filed: Feb. 17, 2017

(86) PCT No.: PCT/CA2017/050213
§ 371 (c)(1),
(2) Date: Aug. 17, 2018

(87) PCT Pub. No.: WO2017/139899
PCT Pub. Date: Aug. 24, 2017

(65) Prior Publication Data
US 2020/0002662 A1 Jan. 2, 2020

Related U.S. Application Data

(60) Provisional application No. 62/297,049, filed on Feb. 18, 2016.

(51) Int. Cl.
*C12M 1/36* (2006.01)
*A61B 5/00* (2006.01)
(Continued)

(52) U.S. Cl.
CPC ........... *C12M 41/48* (2013.01); *A61B 5/0013* (2013.01); *A61B 6/486* (2013.01); *C12M 1/34* (2013.01);
(Continued)

(58) Field of Classification Search
USPC ...................................................... 435/288.7
See application file for complete search history.

(56) References Cited

U.S. PATENT DOCUMENTS 6,759,206 B1 * 7/2004 Rubin ...................... C12Q 1/68
435/174
2010/0062481 A1 * 3/2010 Lange ................ G01N 33/5011
435/174
(Continued)

FOREIGN PATENT DOCUMENTS

EP 0259183 * 3/1988
JP S63158459 * 7/1988
WO WO-2015023658 A2 * 2/2015 ............ C12M 23/12

OTHER PUBLICATIONS

Choudhry, Priya. "High-Throughput Method for Automated Colony and Cell Counting by Digital Image Analysis Based on Edge Detection". Feb. 5, 2016. PLoS One 11(2): e0148469. doi:10.1371/journal.pone.0148469 (Year: 2016).*
(Continued)

*Primary Examiner* — Michael A Marcheschi
*Assistant Examiner* — Nathan G Esperon
(74) *Attorney, Agent, or Firm* — Norton Rose Fulbright Canada LLP

(57) ABSTRACT

A high throughput automated assay platform for temporal image processing of cell growth and colony formation before and after radiation therapy treatments. The platform is designed to compute and monitor a therapeutic protocol by measuring sensitivity of cell growth to treatment based on a radiation therapy protocol. The platform is designed to
(Continued)

detect relationships between the temporal images being tracked to colony formation behaviour.

26 Claims, 20 Drawing Sheets

(51) Int. Cl.

| | |
|---|---|
| *A61B 6/00* | (2024.01) |
| *C12M 1/00* | (2006.01) |
| *C12M 1/34* | (2006.01) |
| *C12M 1/42* | (2006.01) |
| *C12M 3/00* | (2006.01) |
| *G01N 33/50* | (2006.01) |
| *G16H 10/40* | (2018.01) |
| *G16H 10/60* | (2018.01) |
| *G16H 20/40* | (2018.01) |
| *G16H 30/40* | (2018.01) |
| *A61B 34/20* | (2016.01) |

(52) U.S. Cl.
CPC ................ *C12M 1/36* (2013.01); *C12M 1/42* (2013.01); *C12M 23/42* (2013.01); *C12M 31/00* (2013.01); *C12M 41/12* (2013.01); *C12M 41/34* (2013.01); *G16H 10/40* (2018.01); *G16H 10/60* (2018.01); *G16H 20/40* (2018.01); *G16H 30/40* (2018.01); *A61B 2034/2065* (2016.02); *A61L 2202/14* (2013.01); *G01N 33/5011* (2013.01); *G01N 2800/52* (2013.01)

(56) References Cited

U.S. PATENT DOCUMENTS

| | | | | |
|---|---|---|---|---|
| 2011/0171663 | A1 | 7/2011 | Smith et al. | |
| 2011/0216953 | A1* | 9/2011 | Callahan | ................ G16H 30/20 |
| | | | | 382/128 |
| 2012/0148491 | A1 | 6/2012 | Akudugu et al. | |
| 2014/0121495 | A1* | 5/2014 | Dempsey | ............. A61B 5/4878 |
| | | | | 600/1 |

OTHER PUBLICATIONS

Jeffrey Coderre. Cell Survival Curves. "22.55 "Principles of Radiation Interactions"". 2004. Downloaded Oct. 3, 2022. https://ocw.mit.edu/courses/22-55j-principles-of-radiation-interactions-fall-2004/resources/cel_surv_curves/ (Year: 2004).*

Zanoni "3D tumor spheroid models for in vitro therapeutic screening: a systematic approach to enhance the biological relevance of data obtained". Jan. 11, 2016. (Year: 2016).*

Georgantzoglou, Antonios. et al. "Applications of High-Throughput Clonogenic Survival Assays in High-LET Particle Microbeams". Jan. 25, 2016. Front. Oncol. 5:305. doi: 10.3389/fonc.2015.00305 (Year: 2016).*

Choudhry P (2016) High-Throughput Method for Automated Colony and Cell Counting by Digital Image Analysis Based on Edge Detection. PLoS One 11(2): e0148469. doi:10.1371/journal. (Year: 2016).*

Franken, et al. "Clonogenic assay of cells in vitro". Nature Protocols. vol. 1 No. 5, 2006. pp. 2315-2319. (Year: 2006).*

Don Whitley Scientific. "H35 HEPA Hypoxystation". Feb. 2014. http://www.hypoxystation.de/assets/product-pdfs/Whitley%20Workstations/H35_HEPA_Hypoxystation/083_2_H35_HEPA.pdf (Year: 2014).*

Roukos, Vassilis. et al. "Cell cycle staging of individual cells by fluorescence microscopy". Jan. 29, 2015. Nature Protocols, vol. 10, No. 2. doi:10.1038/nprot.2015.016 (Year: 2015).*

Tang, Yangzhong. "A one step imaging assay to monitor cell cycle state and apoptosis in mammalian cells". Mar. 14, 2015. Curr Protoc Chem Biol. ; 6(1): 1-5. doi:10.1002/9780470559277.ch130140. (Year: 2015).*

Guan, Fada. et al. "Spatial mapping of the biologic effectiveness of scanned particle beams: towards biologically optimized particle therapy". May 18, 2015. Rep. 5, 9850; DOI:10.1038/srep09850 (Year: 2015).*

Geissmann Q "OpenCFU, a New Free and Open-Source Software to Count Cell Colonies and Other Circular Objects". (2013) PLoS One 8(2): e54072. doi:10.1371/journal.pone.0054072 (Year: 2013).*

Dittmar et al. "ScreenMill: A freely available software suite for growth measurement, analysis and visualization of high-throughput screen data". BMC Bioinformatics 2010, 11:353 http://www.biomedcentral.com/1471-2105/11/353 (Year: 2010).*

Chalfoun et al. "FogBank: a single cell segmentation across multiple cell lines and image modalities" BMC Bioinformatics (2014) 15: 431 DOI 10.1186/s12859-014-0431-x (Year: 2014).*

Manuel Rodriguez and Robert Jeraj. "Design of a radiation facility for very small specimens used in radiobiology studies". 2008 Phys. Med. Biol. 53 2953 (Year: 2008).*

WIPO, International Search Report and Written Opinion for PCT Application No. PCT/CA2017/050213 dated May 11, 2017.

Zanoni et al., Scientific Reports, Jan. 11, 2016 (Nov. 1, 2016), vol. 6, pp. 1-11, ISSN 2045-2322 [online] [retrieved on May 9, 2017 (Sep. 5, 2017)]. Retrieved from the Internet: <DOI:10.1038/srep19103 (2016)>.

Archibald et al., Biochemical Engineering Journal, Jul. 10, 2015 (Oct. 7, 2015), vol. 108, pp. 69-83, ISSN 1369-703X [online] [retrieved on May 9, 2017 (Sep. 5, 2017)]. Retrieved from the Internet: <http://dx.doi.org/10.1016/j.bej.2015.07.001>.

Extended/Supplementary European Search Report issued in European Application No. 17752613.4, dated Sep. 25, 2019.

Sheppard, D., "Overview of IMRT and Arc-Based Techniques", AAPM Annual Meeting, Jul. 21, 2014, retrieved from the Internet: http://amos3.aapm.org/abstracts/pdf/90-25488-334462-103267.pdf.

European Patent Office, Office Action dated Nov. 23, 2022 in European Patent Application No. 17752613.4.

* cited by examiner

LOAD IMAGE SET — 502

SORT IMAGES BY MICRO WELL IDENTIFIERS — 504

IMAGE PROCESSING FOR EACH WELL — 506

IMAGE PROCESSING FOR TEMPORAL IMAGES — 508

FILTER BACKGROUND FROM IMAGES — 510

FIND CELL CENTROIDS — 512

GROUP CELLS, FIND GROUP CENTROIDS — 514

WRITE GROUP ID, GROUP CENTROID, AND GROUP POPULATION TO FILE — 516

PRIMARY
RADIATION
FIELD

WELL PLATE

COLLIMATOR

DEVICE, SYSTEM AND PROCESS FOR ROBOTIC RADIOBIOLOGY

This application is a U.S. national stage entry, under 35 U.S.C. § 371, of International Application Number PCT/CA2017/050213, filed Feb. 17, 2017, which claims priority benefit of U.S. Provisional Application No. 62/297,049, filed Feb. 18, 2016, the entire contents of each of which are hereby incorporated by reference.

FIELD

The improvements generally relate to the field of radiobiology and in particular to the field of automated cellular radiobiology.

INTRODUCTION

The colony forming assay, or clonogenic assay is a method to produce measurements of survival and proliferation of cancer cells in vitro. Clonogenic assay is the first quantitative measurement of cell survivability by radiation treatment and is also employed to determine the effect of chemotherapeutic agents on tumour cells. The clonogenic assay is a robust method; however it requires significant time and allocation of cell culture and microscopy resources. Other limitations include throughput and a lengthy experimental turnaround of several weeks to grow and count sufficient cell colonies. Previous modifications to the standard assay protocol have focused on improving these challenges using a miniaturized platform containing multi well plates. These modifications necessitate manual investigator intervention for sample preparation.

Radiation treatments on tumour cells will produce single strand and double strand breaks in cell DNA that can trigger cell apoptosis. Apoptosis is not an immediate result of treatment as cells will attempt to repair DNA damage before undergoing division. Cells that complete the repair cycle and divide will exhibit a delay before dividing in comparison to untreated cells. The rate at which a colony grows can then be an indicator of the extent of radiation damage if such a delay is observed. In the standard assay, measurements are typically taken at the beginning and end of the assay and as a result there is limited information available to determine the growth rate. Colonies experiencing growth delay may not reach the minimum population criteria to be defined as a clonogenic colony and may not be scored. In the standard assay, these small colonies are discounted and do not contribute to the overall analysis of cell survivability. Standard measurements in a clonogenic assay estimate the number of cells plated per sample and a count of cells that retain their ability to divide post treatment. The measurements omit clonogenic colony growth dynamics and interactions that may occur between cell treatment and sample fixing.

Cell populations subjected to a particular treatment can be used to produce survival curves that convey a surviving fraction of initial cells as a function of dose (see for example FIG. 11 which illustrates such a graph as an example). The curve is created by plotting the available data and comparing it with educated models for cellular response. Standard measurements in a clonogenic assay however sometimes have the problem that large amounts of data may be collected for parts of the curve that do not require high data resolution while simultaneously insufficient data may be collected for a particular part of the curve that requires higher data resolution. The standard (classical) clonogenic assay protocol, while sufficient for many experiments in biology has several shortcomings when it is used to investigate behaviour which is dependent on a large number of factors, especially when the effect of each factor is not independent. In the classical assay, there is a defined endpoint at which time colonies are counted, usually a fixed time interval after plating of the cells. The use of a fixed time endpoint presents a limitation of the classical clonogenic assay in that it limits the detection of behaviours and events that occur between plating and counting. Also, the arbitrary choice of the set of factors to be investigated in a classical assay presents an additional limitation to the scalability of the experiment should the results from the experiment be unsatisfactory. While the results of a classical assay completed with an arbitrarily chosen set of factors can provide a convenient general result, the ability to detect more subtle behaviour is limited. Furthermore, in a classical assay the cell plating density is chosen arbitrarily, based on empirical data. Using an arbitrary cell plating density for a classical assay investigating a wide range of factors results in a large variation in the number of colonies seen in each well. In some wells with factors that do not impede cell proliferation, the colonies could merge together, and in some wells, there could be zero colonies formed for factors that significantly reduce cell viability. These effects, when combined with the use of a fixed endpoint for cell counting, result in a large experimental uncertainty and hinder reproducibility of experimental results. The classical assay protocol as described is a combinatorial problem that leads to large number of repetitions and time and manual effort.

SUMMARY

In accordance with one aspect, there is provided a high throughput radiobiology assay platform. The assay platform may have a programmable cell loading system for loading concentrations of cells; an imaging interface for receiving temporal images of cells growing in the wells before and after treatment; an image processor for processing the temporal images to detect relations between the images to track colony formation behaviour from said cell growth over time and computing a likelihood of survival of a type of said cells after the treatment to a specific dose; a data storage device for generating and storing data structures for the images and tracked colony behaviour; and a treatment system for triggering delivering of the treatment to said cells based on a treatment protocol for the specific dose, the treatment system capable of applying different treatment doses to different cells or groups of said cells.

In some embodiments, the image processor is further for processing the temporal images of the colony formation to measure sensitivity of said cells to the treatment, the data storage device for storing, in the data structures, the measured sensitivity of said cells to the treatment.

In some embodiments, the assay platform has a radiation delivery device for delivering radiation treatment to said cells as part of the treatment, the image processor for further processing the temporal images to measure sensitivity of said cells to the radiation treatment, the data storage device for storing, in the data structures, the measured sensitivity to the treatment.

In some embodiments, the image processor is further for further processing the temporal images of colony formation to measure sensitivity of said cells to both the treatment and the radiation treatment, the data storage device for storing, in the data structures, the measured sensitivity to both the treatment and the radiation treatment.

In some embodiments, the assay platform has a radiation delivery device is configured to deliver additional treatment to said cells based on the tracked colony formation behaviour.

In some embodiments, the treatment protocol is computed based on the tracked colony formation behaviour.

In some embodiments, the treatment system is configured for delivery of the treatment as an initial treatment and an additional treatment based on the measured sensitivity of said cells to the treatment.

In some embodiments, the treatment protocol is computed based on the tracked colony behaviour.

In some embodiments, the assay platform has an imaging system for generating the temporal images of the colony, the imaging system comprising a programmable microscope capable of generating serial images of said cells in the multi-well plate before and after delivery of the treatment.

In some embodiments, the assay platform has a treatment monitoring unit for processing the data structures to develop the treatment protocol for cell density and treatment delivery and monitoring measured sensitivity of said cells to the treatment.

In some embodiments, the treatment protocol defines a group of cells as a colony using a classifier derived from information about both a number of cells in a certain region of interest and the spatio-temporal history of the cells involved.

In some embodiments, the treatment comprises radiation treatment, drug treatment, additional environment factors, or a combination thereof.

In some embodiments, the assay platform is configured to load a well plate of said cells to match an anticipated dose and survival probability for the treatment.

In some embodiments, the treatment protocol comprises a programmable pattern of radiation dose delivered to wells of said cells based on cell survival and statistical uncertainty.

In some embodiments the choice of which wells on a plate get a treatment protocol's particular radiation dose and well plate loading is randomized.

In some embodiments, the image processor is configured to extract cell locations in the multi-well plate and automatically identify, characterize and localize colonies of the cells.

In some embodiments, the image processor comprises fluorescence to measure said cell growth.

In some embodiments, the cells are loaded into wells of a multi-well plate, the treatment system capable of applying different treatment doses to different wells of the multi-well plate.

In some embodiments, the different treatment doses are based on different treatment rates delivered to each well.

In some embodiments, the different treatment doses are based on different x-ray energies delivered to each well.

In some embodiments, the treatment system may deliver the treatment in the form of x-rays, electrons, gamma-rays, hadrons, or other sources and forms of radiation.

In some embodiments, the cells are loaded into a continuous media or single well plate configuration (e.g. the well plate configuration does not have multiple wells or compartments).

In some embodiments, the treatment protocol comprises patterns of drug dose delivery.

In some embodiments, the treatment protocol comprises patterns of radiation dose delivery.

In some embodiments, the treatment protocol comprises patterns of environmental factors such as oxygen and heat.

In some embodiments, the image interface receives or captures data on changes in the cell growth after the treatment based on analysis of cell growth rate and initial cell cycle position.

In accordance with another aspect, there is provided a high throughput radiobiology assay process comprising: cell culture plating; cell treatment; image acquisition for temporal images of cells growing using an image system; image processing using a processor device with an imaging interface to receive the temporal images, the processing including computing relations between the images to track colony formation behaviour from said cell growth over time; counting verification and plating optimization using the processor device; writing, using the processor device, output data for clone survival to data storage device; and delivering treatment to said cells based on a treatment protocol.

In some embodiments, the image processing comprises sorting the images of the colony formation using the processor device; for each well, for each image associated with the respective well, using the processor device for, removing or filtering background from the image; finding cell centroids; grouping centroids; and writing output data for the image processing to the data storage device, the output data for computing the treatment protocol.

In some embodiments, the image processing comprises measuring sensitivity of said cells to the treatment using the processor device by processing the images of the colony formation; and writing output data for the measured sensitivity of said cells to the treatment to the data storage device, the treatment protocol computed or updated based on the measure sensitivity.

In some embodiments, the process comprises generating the treatment protocol using the processor device and the temporal images of the colony formation; and writing output data for the treatment protocol to the data storage device.

In some embodiments, the process comprises delivering radiation treatment to said cells as part of the treatment, processing the temporal images to measure sensitivity of said cells to the radiation treatment; and storing the measured sensitivity to the treatment to the data storage device.

In some embodiments, the process comprises processing the temporal images to measure sensitivity of said cells to the treatment; and delivering the treatment as an initial treatment and an additional treatment based on measured sensitivity of said cells to the treatment.

In another aspect, there is provided a high throughput radiobiology assay process. The process involves receiving therapeutic parameters and therapeutic protocol. The process involves triggering cell culture seeding using the therapeutic parameters. The process involves executing cell therapeutic protocol. The process involves collecting and processing temporal images of cells growing from an image system, the processing including computing relations between the images to track colony formation behaviour of said cell growth over time using the processor device. The process involves generating model of cell survival from the images. If there is not sufficient resolution in the model of cell survival, the process involves adding additional dose points to the model. The process involves generating an updated seeding and therapeutic protocol. The process involves executing the updated therapeutic protocol to collect and process additional temporal images of the cells from the imaging system. The process involves generating an updated model of cell survival from the images. The process involves writing, using the processor device, output data for clone survival to a data storage device.

In some embodiments, the process involves collecting of the temporal images comprises imaging micro wells, processing the images to count colonies and storing the images and processed data in the data storage device.

In some embodiments, processing the images to count colonies involves filtering noise, counting cells, and grouping the cells into colonies.

In some embodiments, the process involves generating an updated seeding and therapeutic protocol by calculating the number of cells to observe to meet therapeutic parameters; for each dose that requires additional measurements, assigning cells to well and doses to wells, the assigned doses being part of the therapeutic parameters; and seeding cells in the well plate.

In another aspect, embodiments described herein provide a high throughput radiobiology assay process. The process involves plating cell cultures and triggering cell therapy. The process involves collecting temporal images of cells growing from an image system. The process involves processing the images using a processor device with an imaging interface to receive the temporal images, the processing including computing relations between the images to track colony formation behaviour of said cell growth over time. The process involves counting verification and plating optimization using the processor device. The process involves writing, using the processor device, output data for clone survival to data storage device. The process involves delivering therapy to said cells based on a therapeutic protocol.

In some embodiments, the process involves sorting the images of the colony formation using the processor device; for each well, for each image associated with the respective well, the process involves using the processor device for removing or filtering background from the image; finding cell centroids; grouping centroids; writing output data for the image processing to the data storage device, the output data for computing the therapeutic protocol; and correcting for cell seeding multiplicity to measure the probability of survival.

In some embodiments, the process involves measuring sensitivity of said cells to the therapy using the processor device by processing the images of the colony formation; and writing output data for the measured sensitivity of said cells to the therapy to the data storage device, the therapeutic protocol computed or updated based on the measure sensitivity.

In some embodiments, the process involves generating the therapeutic protocol using the processor device and the temporal images of the colony formation; and writing output data for the therapeutic protocol to the data storage device.

In some embodiments, the process involves delivering radiation therapy to said cells as part of the therapy, processing the temporal images to measure sensitivity of said cells to the radiation therapy; and storing the measured sensitivity to the therapy to the data storage device.

In some embodiments, the process involves processing the temporal images to measure sensitivity of said cells to the therapy; and delivering the therapy as an initial therapy and an additional therapy based on measured sensitivity of said cells to the therapy.

In another aspect, there is provided a high throughput radiobiology assay platform that involves an algorithm that predicts the likelihood of survival of a type of cells after irradiation to a specific dose; a programmable cell loading system that is capable of loading various concentrations of cells into the wells of a multi-well plate; a programmable irradiation system that is capable of applying different doses to different wells of a multi-well plate; a programmable microscope that is capable of generating serial images of living cells in multi-well plates before and after irradiation; an image processing chain that can extract cell locations and automatically identify, characterize, and localize colonies of cells; and a data storage device for storing the intermediate and final byproducts.

Many further features and combinations thereof concerning embodiments described herein will appear to those skilled in the art following a reading of the instant disclosure.

DESCRIPTION OF THE FIGURES

In the figures.

DETAILED DESCRIPTION

Figure 1:
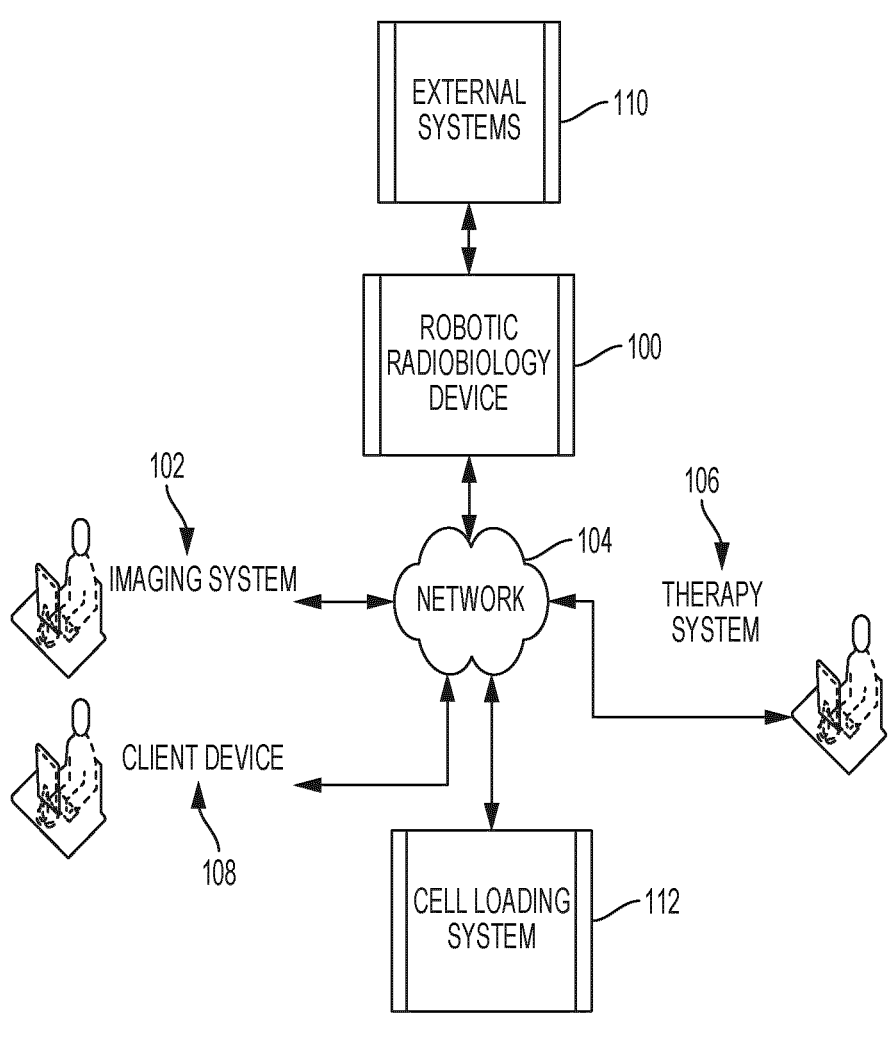
FIG. 1 is a view of an example system for an automated high throughput clonogenic assay.

Embodiments described herein relate to devices, systems, and processes for robotic radiobiology to provide a high throughput automated assay platform. Embodiments described herein relate to developing an automated high throughput clonogenic assay to optimize radiation therapy and drug delivery using computed and monitored treatment protocols. Therapy may involve irradiation only or irradiation in combination with drug or microenvironment. The automated high throughput clonogenic assay platform may provide optimized cell seedings using recursive cell plating optimization. The automated high throughput clonogenic assay platform may provide increased temporal resolution for assay monitoring and increased counting precision and accuracy. Further, the automated high throughput clonogenic assay platform may provide increased read out mea-suring cell survival (e.g. colony growth over time, cell proliferation over time, analysis of small colonies-col<50 cells). Standard manual assay techniques may need to opti-mize cell plating density continually and may be labour intensive, time consuming, and at a fixed point in time.

Embodiments described herein relate to devices, systems, and processes for optimizing radiobiology within predefined statistical parameters. There is a large number of possible permutations for radiobiology experiments and therefore experiment design should be efficient and recursive, and with automated implementation. Embodiments described herein relate to devices, systems, and processes that imple-ment a recursive method. Embodiments can break down the problem (building cell survival curves) into parts to inform the whole outcome. First embodiments can gain statistical confidence in the measurements, then check to see if they satisfy some model. If a model is not satisfied by the data, we identify regions where more data can inform a better model and call back the steps to explore this part of the curve. Parts of the method may be iterative, but as a whole it is recursive.

High throughput cellular assays may be implemented on multi-well microplates to identify parameters to predict radiation sensitivity and various chemical treatments. For experiments, colonies for tissue cells may be grown, fixed and stained following incubation and then may be imaged. The images may be analyzed using a process to count colonies from counts performed using specialized software developed on platforms such as, for example, the Developer Toolbox software by GE Healthcare. Known investigative methods may require manual sample preparation before analysis can be conducted. The manual analysis may also be confined to a fixed point in time to provide cell character-izations. Known approaches may have restricted dynamic range resulting from the increased variability of colonies observed due to spatial restrictions in colony growth.

Embodiments described herein relate to devices, systems and processes for automated, robotic cellular radiobiology using temporal images of colonies of tissue cells. In addition to modelling cell therapy, increased temporal sampling of cellular growth and optimizations in cell seeding can improve colony detection and provide additional cell sur-vival information. Embodiments described herein provide an automated image analysis process that improves the efficiency of performing clonogenic assays and other example improvements as described herein.

Embodiments described herein provide a high throughput automated assay platform with time lapse imaging and processing that computes relations between the images through time to track colony behaviour and to write data structures of such output data. The proposed system may process images to compute how the clones develop through time and measure their sensitivity to therapy and store the results in a data structure. The process may mine stored data to design an improved experimental protocol for cell density and therapy delivery. As noted, therapy may involve irra-diation only or irradiation in combination with drug or microenvironment.

FIG. 1 is a view of an example system for an automated high throughput clonogenic assay with a robotic radiobiol-ogy device 100 according to some embodiments. The device 100 automates a clonogenic assay completed on well micro-plates, or other media, employing automated image analysis. The device 100 implements rapid cell and colony detection with additional temporal parameters which are not available to the standard assay. The image analysis process may produce cell and colony counts to greater precision than counting by eye, for example. The time dependent param-eters available to the described high throughput clonogenic assay are beyond the capabilities of the standard assay process. The time lapse image series have captured colony growth information while image processing enables the analysis of multiple parameters to provide a higher order measurement of the effects of therapy.

Figure 11:
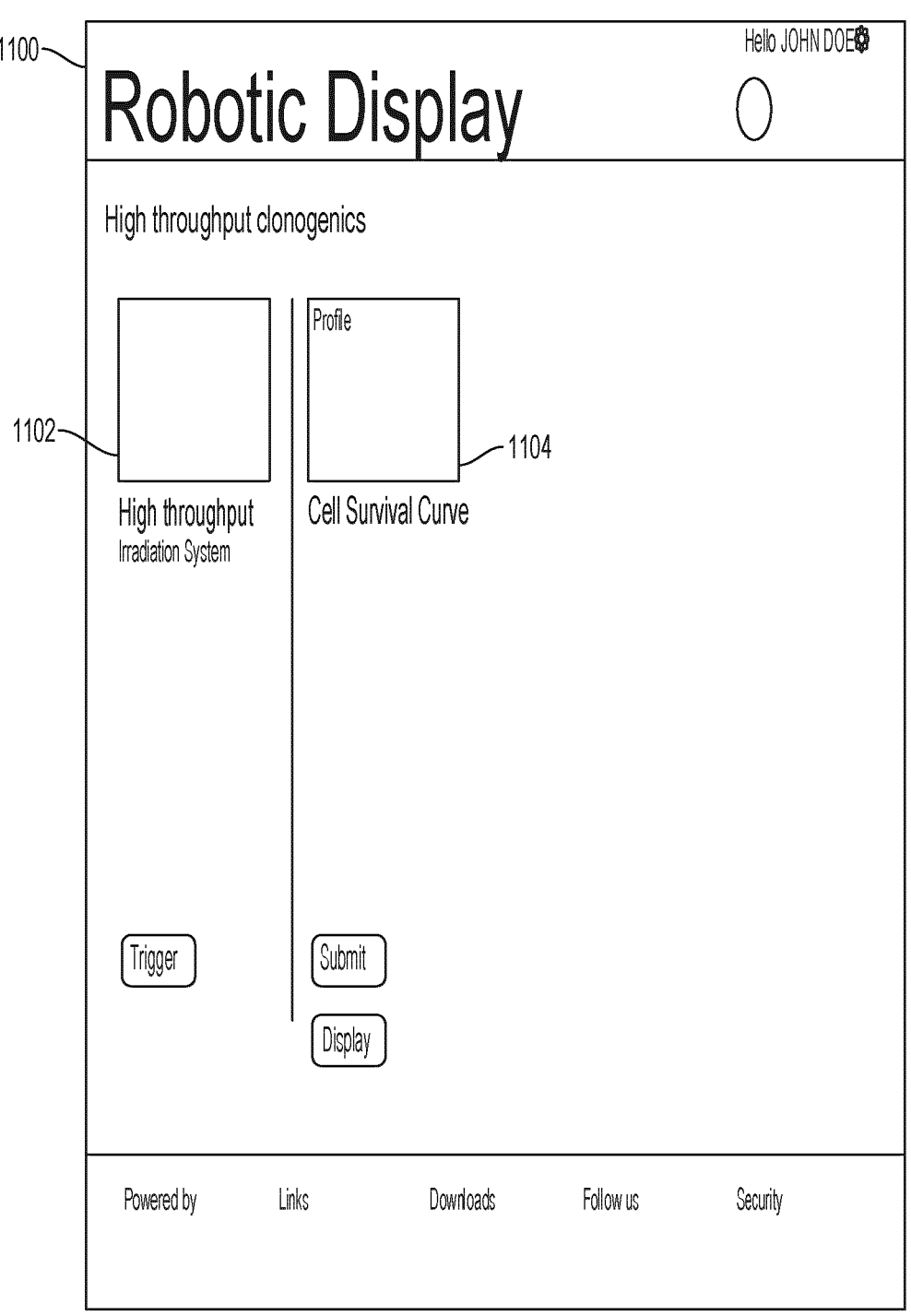
FIG. 11 is a view of an example interface.

The device 100 interfaces with external systems 110 to receive images, transmit control commands and data, exchange therapy data, and so on. The device 100 couples to an imaging system 102 to receive temporal images. The imaging system 102 includes an image acquisition unit for different imaging modalities. The device 100 couples to a therapy system 106 for acquiring therapy data for monitor-ing sensitivity to therapy delivery. The device 100 may connect directly to other components and may also use network 104 to establish network connections. The device 100 couples to a client device 108 to generate and control an interface for clonogenic assay data. FIG. 11 is a view of an example interface. The device 100 may connect directly to cell loading system 112 configured to load various concen-trations of cells into the wells of a multi-well plate.

Figure 2:
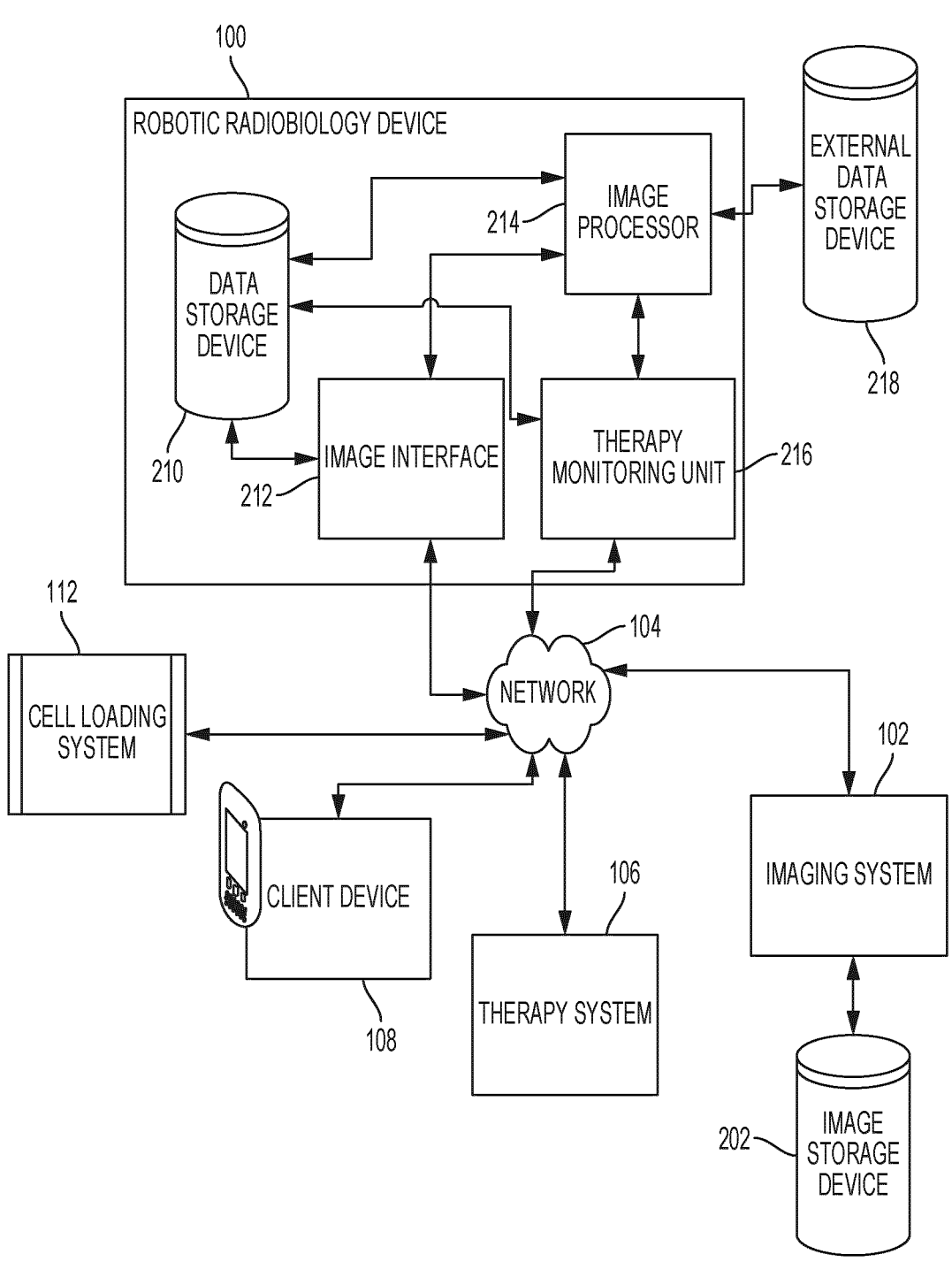
FIG. 2 is a view showing an alternate example system for an automated high throughput clonogenic assay.

FIG. 2 is a view showing an alternate example system for an automated high throughput clonogenic assay with a robotic radiobiology device 100 according to some embodi-ments. The device 100 includes an imaging interface 212 for receiving temporal images of cells growing from imaging system 102 which may have an image acquisition unit, a connection to an internal or external image storage device 202, or other access port to temporal image data. Cells grow or form into colonies, which may be referred to as colony formation. The device 100 has an image processor 214 for processing the temporal images to detect relations between the images to track colony formation behaviour from the cell growth over time. The device 100 has a data storage device 210 for generating and storing data structures for the images and tracked colony behaviour.

The device 100 couples to a therapy system 106 for delivering radiation therapy or drug delivery therapy to the plated cells. The imaging system 102 generates additional temporal images over time during therapy. The imaging interface 212 receives the additional images and the image processor 214 processes the temporal images of the colony formation to measure sensitivity of the cells to the therapy. The data storage device 210 stores, in data structures, the measured sensitivity to the therapy for subsequent retrieval, analysis and transmission. The therapy system 106 may, for example, include a radiation delivery device for delivering radiation therapy to the plated cells. The device 100 may generate an optimized therapy protocol to configure and control the therapy system 106 for delivery of the therapy, for example. The therapy protocol may be based on the tracked colony formation behaviour, relations between the images, sensitivity to the therapy, and other data computed by the image processing as further described herein, such as in relation to FIGS. 6, 7 and 8, for example. The therapy protocol may be refined or updated by monitoring the impact of the therapy or sensitivity of the cells to the therapy. If too many cells are seeded or if too much dose is delivered then the resulting data may be useless and therefore a region for experimentation can be in the range of intermediate dosing and seeding. Furthermore, certain areas of the survival curve can be underpopulated and may need to be bolstered with more data to increase resolution.

The device 100 has a therapy monitoring unit 216 to compute or update the therapy protocol and to process the image processing results or the data structures of the tracked colony behaviour to develop the therapy protocol for cell density and therapy delivery. The therapy monitoring unit 216 monitors the measured sensitivity of the cells to the therapy. Accordingly, embodiments described herein may provide therapy delivery combined with ability to directly monitor the impact of the therapy on the cell growth or colony formation. Embodiments may deliver therapy as radiation therapy, with the possibility of also combining radiation and chemotherapy therapy or other drug delivery or therapy techniques. The therapy may involve an initial therapy and further or additional therapy after the initial therapy. The further therapy may be based on the monitored or measured sensitivity to the initial therapy.

In some embodiments, the image processor 214 processes the temporal images of the colony formation to measure sensitivity of said cells to the therapy. The data storage device 218 stores, in data structures, the measured sensitivity of said cells to the therapy. The measured sensitivity may be used for the monitoring the therapy.

In some embodiments, the therapy system 106 may include various components to provide different types of therapy. In some embodiments, the therapy comprises radiation therapy, drug therapy, additional environment factors, or a combination thereof.

For example, therapy system 106 may have or couple to a radiation delivery device for delivering radiation therapy to said cells as part of the therapy. The image processor 214 processes the temporal images to measure sensitivity of said cells to the radiation therapy, and the data storage device 210 stores, in the data structures, the measured sensitivity to the radiation therapy. In some embodiments, the image processor 214 is further for processing the temporal images of colony formation to measure sensitivity of said cells to both the therapy and the radiation therapy. The data storage device 210 stores, in the data structures, the measured sensitivity to both the therapy and the radiation therapy. In some embodiments, the therapy system 106 may include a radiation delivery device is configured to deliver additional therapy to said cells based on the tracked colony formation behaviour.

In some embodiments, the therapy system 106 is configured for delivery of the therapy as an initial therapy and an additional therapy based on the measured sensitivity of said cells to the therapy.

In some embodiments, the imaging system 102 has a programmable microscope capable of generating serial images of said cells in the multi-well plate before and after delivery of the therapy. In some embodiments, the imaging system 102 comprises fluorescence to measure said cell growth.

In some embodiments, the device 100 has a therapy monitoring unit 216 for processing the data structures to develop the therapy protocol for cell density and therapy delivery and monitoring measured sensitivity of said cells to the therapy. In some embodiments, the therapy protocol is computed based on the tracked colony formation behaviour. In some embodiments, the therapy protocol defines a group of cells as a colony using a classifier derived from information about both a number of cells in a certain region of interest and the spatio-temporal history of the cells involved. In some embodiments, the therapy protocol comprises a programmable pattern of radiation dose delivered to wells of said cells based on cell survival and statistical uncertainty. In some embodiments, the cells are loaded into a continuous media single well plate configuration instead of using a multi-well plate configuration. In some embodiments, the therapy protocol comprises patterns of drug dose delivery. In some embodiments, the therapy protocol comprises patterns of radiation dose delivery. In some embodiments, the therapy protocol comprises patterns of environmental factors such as oxygen and heat. In some embodiments the therapy protocol comprises an automatically generated and dynamically optimized radiation dose and cell seeding plan based on satisfying the requirements of statistical distributions related to cell survival fraction and other cell therapy response metrics.

In some embodiments, the device 100 is configured to load a well plate of said cells to match an anticipated dose and survival probability for the therapy.

In some embodiments, the image processor 214 is configured to extract cell locations in the multi-well plate and automatically identify, characterize and localize colonies of the cells.

In some embodiments, the cells are loaded into wells of a multi-well plate and the therapy system 106 is capable of applying different therapy doses to different wells of the multi-well plate. In some embodiments, the different therapy doses are based on different therapy rates delivered to each well. For example, different dose rates may be used as biology may change with dose rate at Gy/min. In some embodiments, the different therapy doses are based on different x-ray energies delivered to each well, such as 50 kVp to 250 kVp. In some embodiments, the therapy system 106 may deliver the therapy in the form of x-rays, electrons, gamma-rays, or hadrons, or other sources and forms of radiation.

In some embodiments, the image interface 212 receives or captures data on changes in the cell growth after the therapy based on analysis of cell growth rate and initial cell cycle position. For example, the process may capture data on changes in cell growth after irradiation through analysis of individual cell doubling times and initial cell cycle position.

Figure 3:
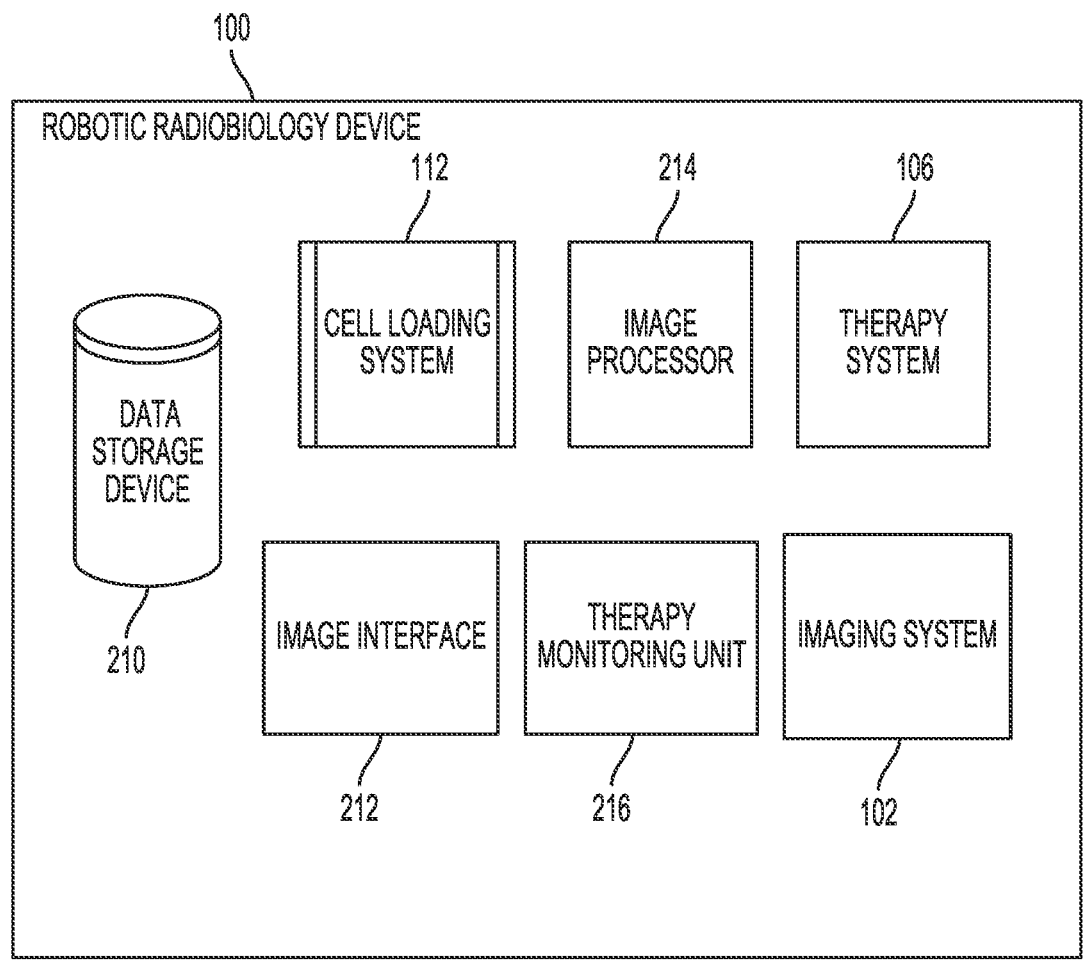
FIG. 3 is a view showing an alternate example system for an automated high throughput clonogenic assay.

FIG. 3 is a view showing an alternate example system for an automated high throughput clonogenic assay with a robotic radiobiology device 100 according to some embodiments. As shown, in some embodiments, device 100 may incorporate the therapy system 106 and the imaging system 102. Other components of FIG. 2 may also couple to device 100 in example embodiments.

For example, the device 100 may provide a high throughput radiobiology assay platform. The device 100 may implement a process that predicts the likelihood of survival of a type of cells after irradiation to a specific dose. The device 100 may a programmable cell loading system 112 that is capable of loading various concentrations of cells into the wells of a multi-well plate. The device 100 may have a programmable irradiation system (e.g. part of therapy system 106) that is capable of applying different doses to different wells of a multi-well plate. The imaging system 102 may have a programmable microscope that is capable of generating serial images of living cells in multi-well plates before and after irradiation. The image processor 214 can extract cell locations and automatically identify, characterize, and localize colonies of cells. The data storage device 210 may store the intermediate and final by products of the process. There may be differential loading of the wells to match the anticipated dose and survival probability. The matching of the cell loading to the dose may be applied in a single well-plate, for example. Loading may be done manually or through a robotic system in example embodiments. For example, loading may be first done based on prior data and then may be re-done based on actual data from the images. In some examples, there may be a programmable pattern of radiation dose delivered to wells filled with cells according to a prescribed algorithm based on cell survival and statistical uncertainty.

Figure 4:
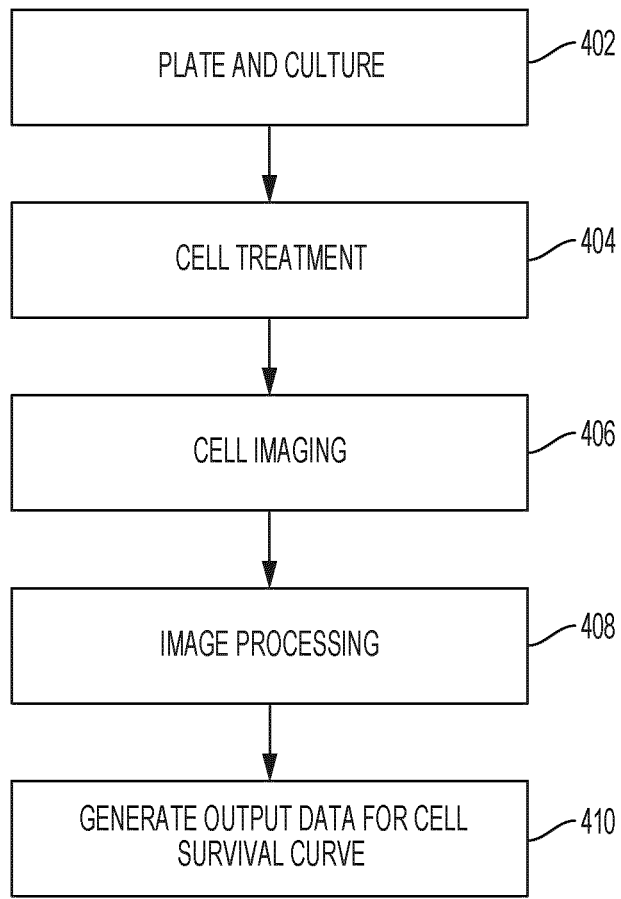
FIG. 4 is a view of an example process for an automated high throughput clonogenic assay.

FIG. 4 is a view of an example process for an automated high throughput clonogenic assay.

At 402, the process involves device 100 generating the plating and cell seeding plan, and performing the plating and seeding of the cells in the micro-wells.

As an illustrative example experiment, a cell line HCT-1 16 H2B RFP may be a colon cancer cell line. Cell media may be mixed using an RPMI 1640 solution with 10% fetal bovine serum (FBS). Cells may be trypsinized and placed in a 5 cells/μL dilution. The well microplates in the experiment may be Corning™ 384 Well Microplates with a working volume of 50 μL. Cells may be seeded at known densities in a 384 well microplate and the remainder of the working volume is filled with the cell media solution. Cells may be allowed 2 hours to incubate at 37° C. to allow cells to settle and to adhere to the well surface.

At 404, device 100 triggers cell therapy with targeted irradiation therapy, drug delivery, or other therapy. At 406, the temporal images of the cells are generated. At 408, the temporal images are processed by device 100 as described herein. At 410, device 100 generates output data for the processing results for storage in data storage devices as data structures. For example, the output data may include data for a cell survival curve.

Figure 5:
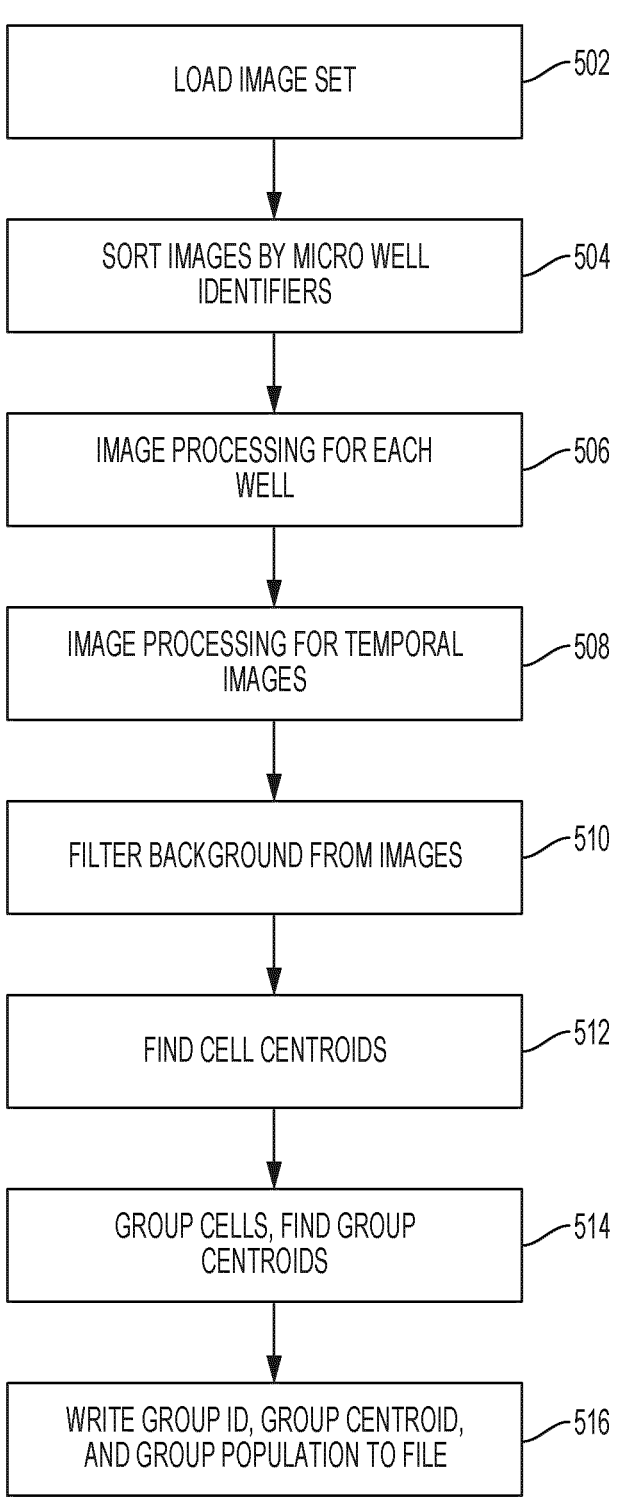
FIG. 5 is an example process of image collection and analysis for an automated high throughput clonogenic assay.

Further details of image processing are shown in FIG. 5. At 502, the device 100 loads the temporal images. At 504, device 100 sorts the images by micro well identifiers. At 506, device 100 executes image processing routines to review each identified well (e.g. well 1 to 384 by increments of 1). For each well, at 508, the image processing reviews images (e.g. image 1 to end by increments of 1) temporally separated by a defined time period (e.g. separated by four hours). At 510, the process filters or removes background from the images, at 512, detects or locates the cell centroids, and at 514, groups the cells and finds the group centroids. At 516, the process issues write commands to data storage devices to update data structures with group identifiers, group centroids, and group population, for example.

Figure 6:
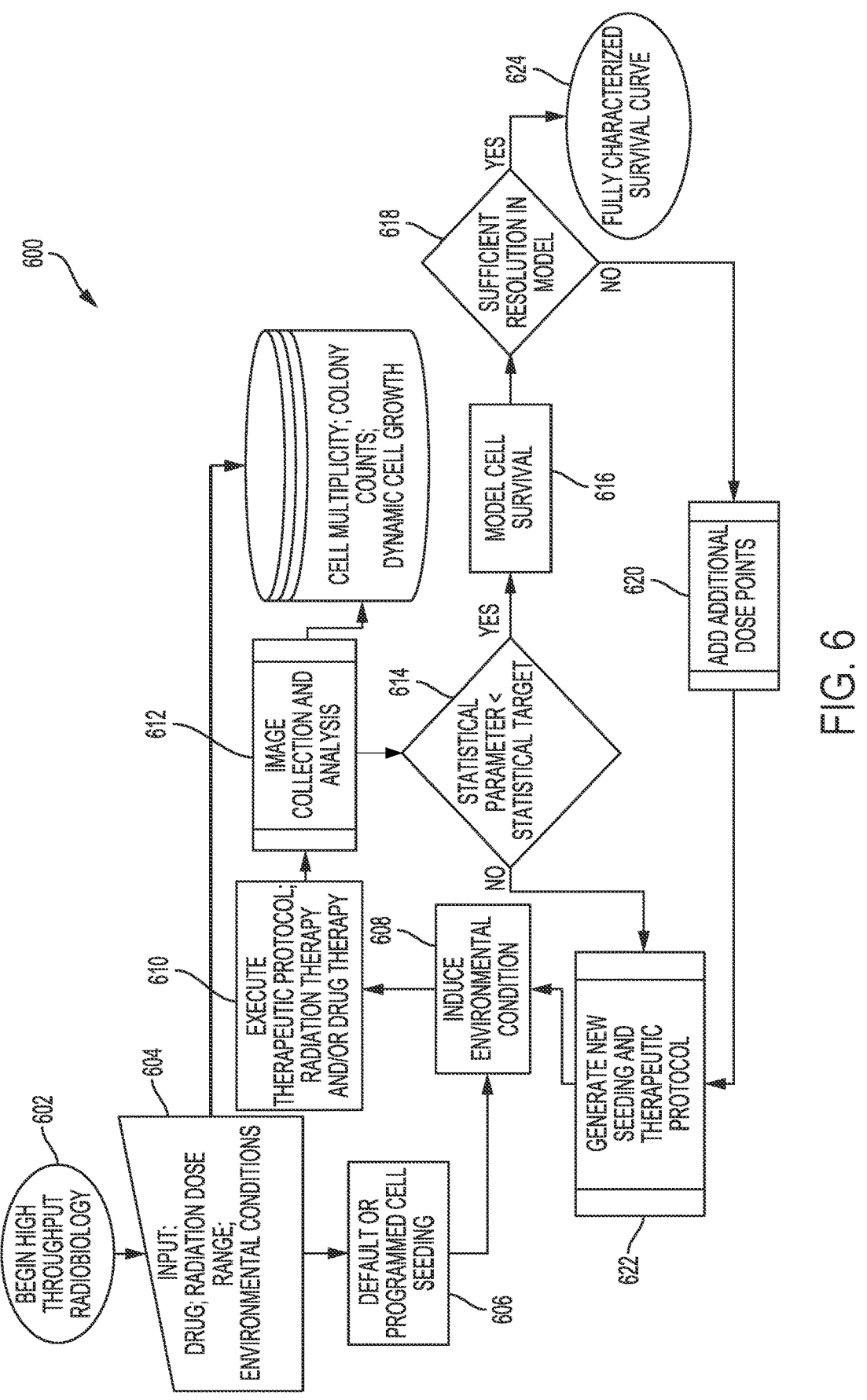
FIG. 6 is a view of an example process for an automated high throughput clonogenic assay.

FIG. 6 is a view of an example process 600 for an automated high throughput clonogenic assay. The process 600 (or portions thereof) may be executed by device 100 in some embodiments. Therapeutic parameters are input into the device 100 and an experimental plan is generated, and executed.

At 602, device 100 begins high throughput radiobiology. This may involve interactions with cell loading system 112, external systems 110, imaging system 102, and client device 108. At 604, device 100 receives as input different therapeutic parameters including drug type, dose parameters, radiation dose rate, and environmental conditions. At 606, device 100 interacts with cell loading system 112 for default or program cell seeding. Default cell seeding patterns may include seeding the same cells for all conditions, or with increasing densities in conditions where cell kill is expected. A seeding pattern may follow a pattern described by FIG. 10. At 608, device 100 induces environmental condition. An example of a condition being applied is exposing cells to 0.2% $O_2$ by volume. Cells may require exposure for to an environment at 0.2% $O_2$ for a period of time to allow dissolved oxygen to dissipate from the media. At 610, device 100 triggers the therapy system 106 to execute the therapeutic protocol for radiation therapy and/or drug therapy. At 612, device 100 collects images and processes the images for therapeutic analysis. An image processing sequence may include steps to remove noise before counting cells and grouping detected cells into colonies (process 702). An image processing sequence of process 704 may include filtering background noise from an image using known image processing techniques, such as a Gaussian filter, and/or a median filter. Cell counting may be performed using a circle Hough transform to detect cell centroids. Cell centroids may be classified as a unit of a group satisfying a minimum separation criterion. Separation criteria might be defined as twice the mean cell diameter. Colonies may be defined as groups comprising of greater than or equal to 50 units. The images and processed data are stored in a data storage device. The images and process data can include cell multiplicity metrics, colony counts, metrics, and dynamic cell growth metrics. FIG. 15 is an example of extracted cell features, where cell centroids are identified and where cells are grouped based on a distance metric. At 614, the device 100 determines whether the statistical parameter is less than a statistical target.

Statistical analysis may involve describing the experiment using binomial counting statistics. Assayed cells are counted to have either formed a colony (survived therapy), or to have not formed a colony. This describes a binomial problem. A binomial problem may be described using a probability density function of the form $$P(n, k) = \binom{n}{k} p^k (1 - p)^{n-k} \qquad \text{[Equation 1]}$$

Where p may refer to the probability of n cells forming k colonies. The probability of forming a colony may be dose dependent. The number of colonies counted may be described as the mean, or expected number colonies, as described by the binomial distribution $$C = N\,P \qquad \text{[Equation 2]}$$

where C may be the expected number successful events, colonies, given N observed cells. The standard clonogenic assay describes this parameter, P, as the plating efficiency. There is also an associated relative standard deviation in the expected number of colonies described by $$\frac{\sigma_b}{c} = \frac{\sqrt{Np(1 - p)}}{Np} \qquad \text{[Equation 3]}$$

A statistical target (ε) may be a target minimized relative standard deviation. Each data point may be assessed to have a relative standard deviation no greater than 10%, or by some other value determined by the user. If the relative standard deviation of the number of colonies counted for a given dose is greater than the statistical target more cells must be plated for that data point. Process 622 describes a method that determines the number of observations required to satisfy the statistical target, $N_b$, is given by $$N_b = \frac{1 - p}{\epsilon^2 p} \qquad \text{[Equation 4]}$$

The number of cells to plate, $N_{plate}$, in the next experiment may be the difference between the cells observed and the cells required to reach the statistical target. These cells may be distributed in 1 or multiple multi-well plates.

$$N_{plate} = N_b - N \qquad \text{[Equation 5]}$$

If the statistical target is satisfied, at 616, device 100 determines model cell survival at 618, device 100 determines whether there is a sufficient resolution in the model. If so, at 624, therapy system 106 fully characterized the survival curve and generates visual elements representing the curve and therapeutic protocol at interface of client device 108. If the device 100 determines that there is not a sufficient resolution in the model then, at 620, device 100 adds additional dose points. At 622, device 100 generates new seeding and therapeutic protocols. Process 1002 is an example process for identifying regions of poor resolution may consist of using the squared residuals, defined as the squared difference between the data points and the model. Data points with large squared residuals can be identified as a point of poor fit. To check if the data point is an outlier, new dose points are assayed. For example: consider a set of dose points: 0, 0.25, 0.5, 1, 2, 4, and 6 Gy whose squared Pearson residuals from fitting a curve are 0, 2.70, 17.75, 0.23, 9.01, 0.68, and 4.05. A residual threshold may be set to decide if a data point is an outlier. Such a threshold may be defined as greater than some value, 4. The data points at 0.5 Gy and 2 Gy may be identified as being outliers. Data points may be added around the identified dose points at the midpoints between currently existing data. In the provided example doses of 0.33 Gy, 0.75 Gy, 1.5 Gy, and 3 Gy may be assayed. Expected survival probabilities can be inferred from the model to estimate the number of cells to observe to achieve the statistical target for each data point as previously described in Equation 4. The process continues, at 608, and therapy system induces environmental conditions and continues the process. A challenge for high throughput assay analysis is that there are a high number of potential permutations and combinations within the data set to generate a model. Systems and methods described herein provide a recursive approach to get a good data set with a fully characterized survival curve. The device 100 determines whether the sufficient resolution in the model and if not continues to add additional dose points at 620 and repeat the model process. If data points are identified the outliers then this may be detected by adding additional dose points. At 614, device 100 checks the statistical uncertainties of each data point and plans the number of observations required to reach an acceptable limit within the target.

Figure 7:
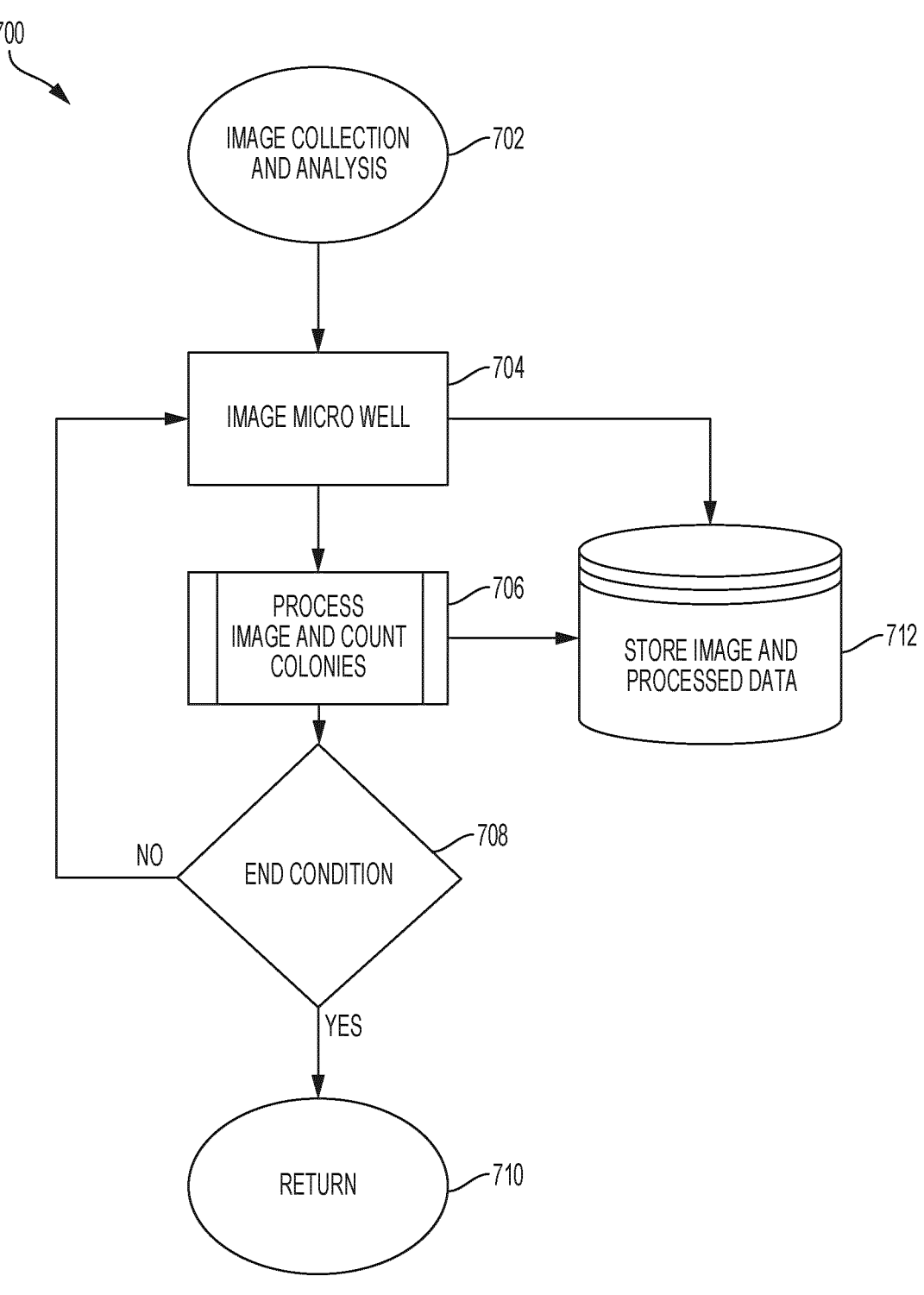
FIG. 7 is an example process of image collection and analysis for an automated high throughput clonogenic assay.

FIG. 7 is an example process 700 of image collection and analysis for an automated high throughput clonogenic assay. In some embodiments, the process 700 can be used by device 100 for image collection and analysis (e.g. at 612 FIG. 6). At 704, the device 100 collects images of the micro well. At 706, therapy system 106 processes the images and counts the colonies. The device 100 stores the images and process data at 712. At 708, device 100 determines whether it has finished processing images for all micro wells and if not returns to 704 to collect additional images of the micro wells. At 710, device 100 compares the statistical parameter to the statistical target.

Figure 8:
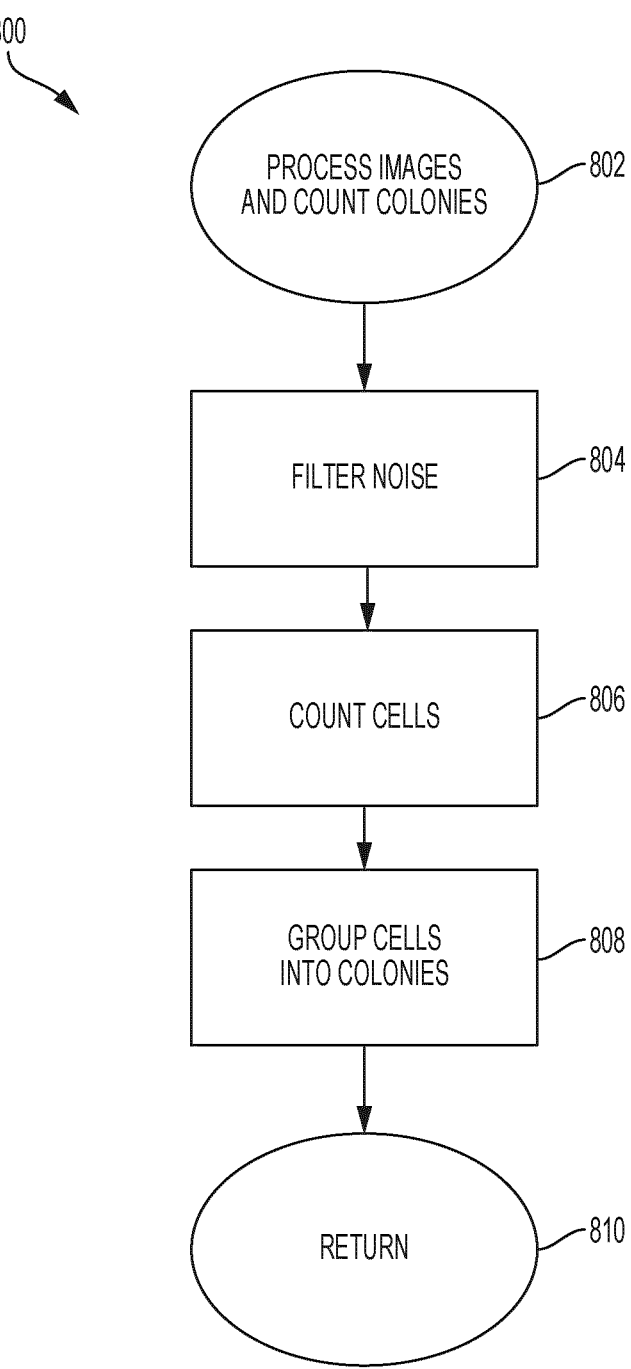
FIG. 8 is an example process to perform digital image analysis.

FIG. 8 is an example process to perform digital image analysis. The process 800 can be used to image micro wells and collect those images for processing (e.g. 704 of FIG. 7). At 802, device 100 processes the images and counts the colonies. At 804, therapy system 106 filters noise from the images. At 806, device 100 counts cells using the filtered images. At 808, device 100 group cells into colonies. At 810, device 100 proceeds to process the images and count the colonies.

Figure 9:
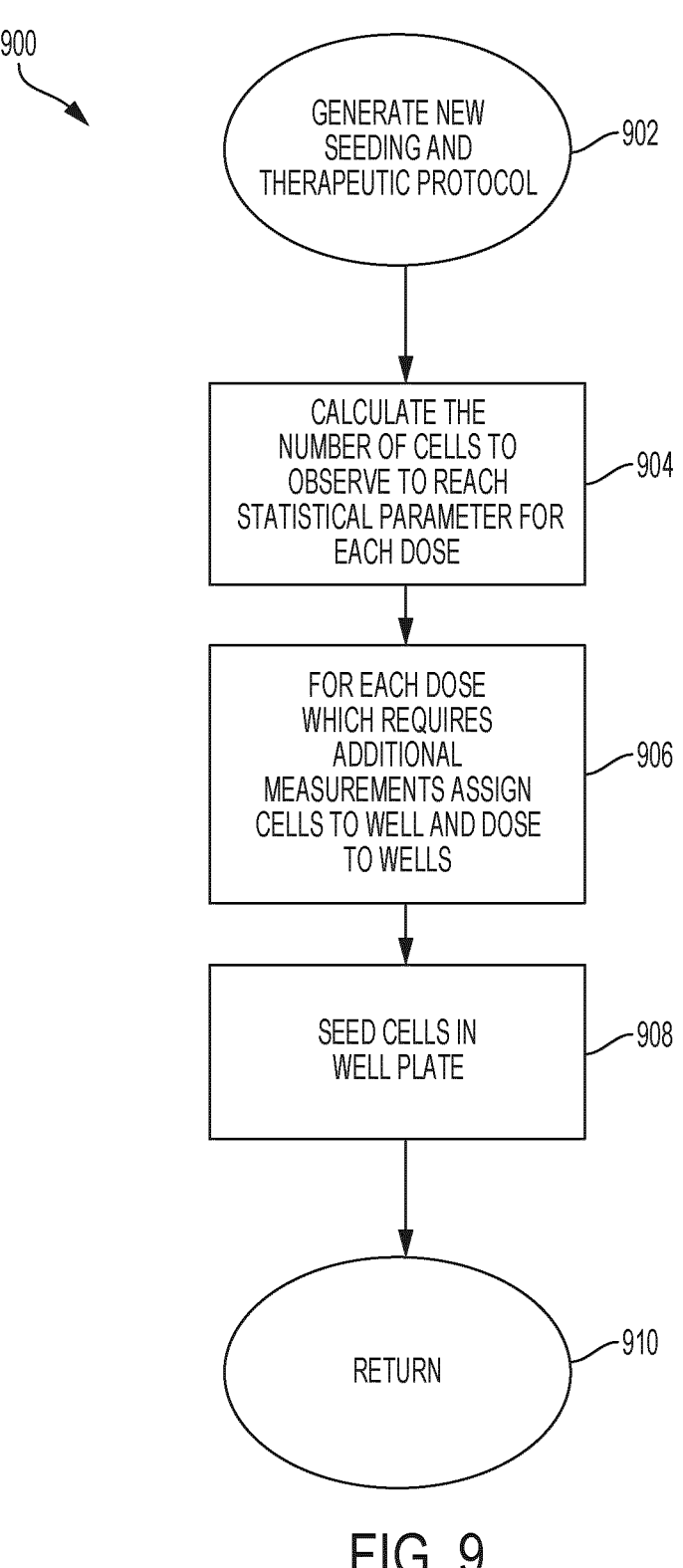
FIG. 9 is an example therapy and seeding protocol generating process to determine the number of cells required for observation to achieve a statistical target for each data point.

FIG. 9 is an example therapy and seeding protocol generating process to determine the number of cells required for observation to achieve a statistical target for each data point.

In some embodiments, device 100 can implement process 900 to generate new seedling and therapeutic protocols (e.g. at 622 of FIG. 6). At 902, device 100 generates new seeding and therapeutic protocols. At 904, device 100 calculates the number of cells to observe to reach a statistical parameter for a particular therapeutic dose D. At 906, for each dose which requires additional measurements, device 100 assigned cells to wells and therapeutic doses to the wells. At 908, device 100 seed cells in the well plate. At 910, device 100 proceeds to induce environmental conditions.

Figure 10:
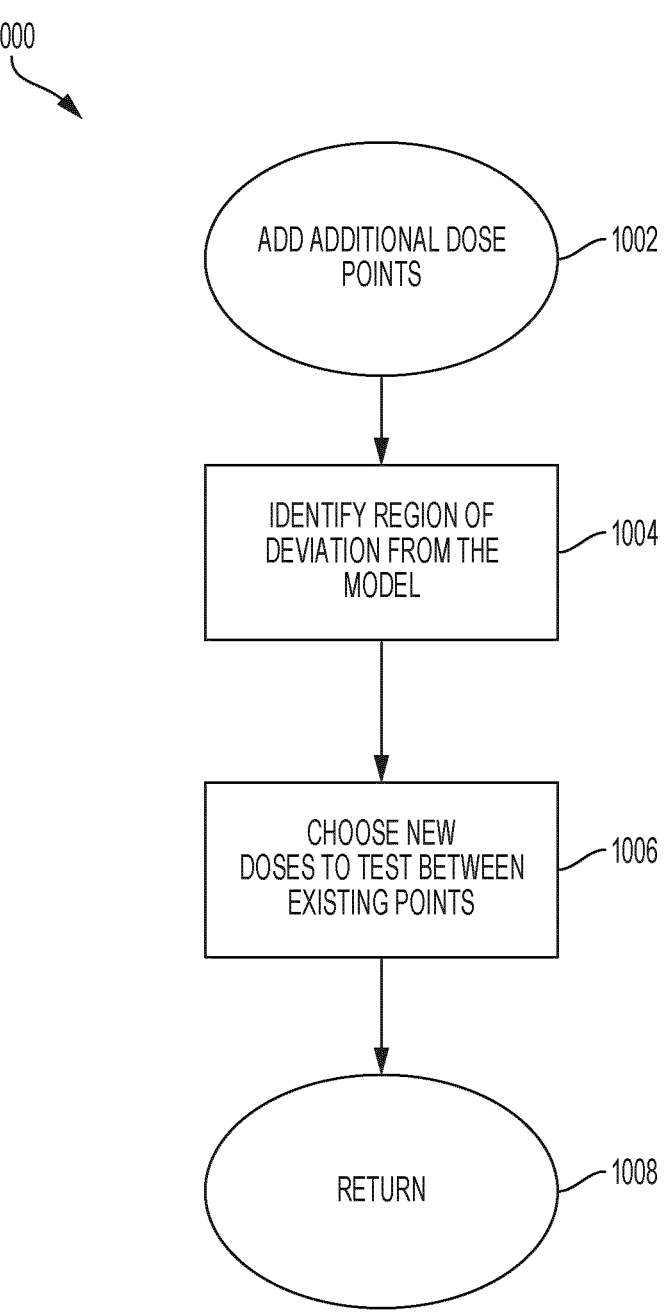
FIG. 10 is an example process for identifying regions of poor data resolution.

FIG. 10 is an example process for identifying regions of poor data resolution. In some embodiments, device 100 can implement process 1000 to add additional dose points (e.g. at 620 of FIG. 6). At 1002, device 100 adds additional dose points to the model. At 1004, device 100 identifies regions of deviation from the model. At 1006, device 100 chooses new doses to test between existing data points. At 1008, device 100 proceeds to generate new seeding and therapeutic protocols.

FIG. 11 illustrates an interface 1100 to generate and display visual elements 1102, 1104 relating to the fully characterized survival code, images, process data, portions of the model, and so on. The device 100 can control components of interface and receive commands at interface.

As an illustrative example experiment, the well microplate may be exposed to a low oxygen, hypoxic, environment (e.g. in a H35 Hypoxystation™, Don Whitley Scientific) and/or targeted irradiation in the X-RAD™ cabinet irradiator (e.g. Precision X-ray). Well microplates may be exposed to a low oxygen environment and sealed within a chamber to maintain the hypoxic condition during irradiation. The irradiator may have a 3 axis motor-driven stage. An irradiator (x ray) has an x-ray tube. The beam is collimated with an 8 mm×12 mm collimator to deliver radiation to 2×3 wells groups in the microplate: the x-ray beam, generated with a tube voltage and current of 225 kV and 13 mA, may deliver radiation at a dose rate of 2.424 Gy/min. Wells may be grouped to decrease irradiation time of the microplate, minimizing the time the cells spend outside of the incubator. The plates may be transported through the radiation beam on a removable stage. The microplate insert may have two pins to ensure the microplate origin in the X-RAD™ coordinate system is consistent. The position of the wells on the plate could then be translated to an X-RAD™ coordinate to create a therapeutic protocol and pilot the plate through the X-ray beam.

A well plate housing chamber can be mounted to the X-RAD™ stage to allow plates to be irradiated from below. The cells are adhered to the polystyrene microplate. Well plate dosimetry may be performed using Gafchromic™ EBT2 radiochromic film following the protocol. Films were adhered to the bottom of the microplate, recording the radiation deposition at the cell layer, and the top, recording the beam exiting the microplate. Beam exit dosimetry films may be used to confirm the beam coverage across the well microplate. EBT2 films may be scanned pre and post exposure on an Epson™ document scanner. The microplate may be irradiated at 6 groups of 48 wells receiving 0.25, 0.5, 1, 2, 4, and 6 Gy with 96 control wells receiving no radiation.

Radiochromic films may be analyzed to measure the mean and variance of dose. Region of interest (ROI) may be selected to look at the $$\text{Flatness} = \frac{D_{max} - D_{min}}{D_{max} + D_{min}} \text{ and Symmetry} = \frac{1}{N}\sum_{i=1}^{N} \frac{D_{N+i} - D_{N-i}}{D_{N+i} + D_{N-i}}$$

of dose distribution across individual wells.

A dosimetric model may be constructed by device 100 to characterize the distribution of radiation dose delivered to the well plate. Doses may be assigned to the well plate to minimize out-of-field dose delivered to neighboring wells.

As noted, the process involves generating temporal images at 406 (FIG. 4). An example may involve fluorescent microscopy or other methods used to measure the cells.

As an illustrative example experiment, irradiated cells may be brought to the IncuCyte Zoom™ microscope to acquire time lapse images of cell growth. Each well on the microplate may be imaged at 3 hour intervals using a 4× objective creating images with 2.42 micrometer pixel size. Fluorescent and phase images may be stored in a local 10 TB hard drive. HCT-1 16 H2B RFP may have a measured doubling rate of approximately 16 hours. Cells may be allowed to grow in the IncuCyte™ for 300 hours; fluorescent image sets may be converted to RGB color images to be exported for image analysis. The cells may be modified to express RFP in the nucleus. RFP may be excited by 488 nm or 532 nm lasers and may have an emission peak of 588 nm.

As noted, the process involves processing temporal images at 408 (FIG. 4).

As an illustrative example experiment, MATLAB™ (MathWorks™) may be chosen with the Image Processing Toolbox as an image processing environment or platform. The device 100 filters noise and performs cell and colony counting. The device 100 extracts cell features and groups cells from a rule set. Colonies may be counted when the population of a group met or exceeded a threshold number of cells, such as, for example, 45 cells. Convention may consider colonies to be composed of at least 50 cells; however, a counting error of cells may be allowed for colony detection, such as, for example, 5 cells. Cells may be grouped based on their spatial separation. It may be assumed that as cells divide, the daughters do not separate by more than 4 cell radii. For example, an HCT-116 cell nucleus has a diameter of 10 $\mu\eta$i; therefore, cell centroids separated by <30 $\mu\eta$i are grouped. The defined time period for temporal resolution (e.g. three hours) provides the opportunity to measure several other factors that are beyond the capability of the standard colony forming assay and may provide total cell proliferation in the entire well and colony growth over time. All metrics used for automated cell counting may be validated against manual counts and other tissue analysis software (e.g. Definiens™ Developer XD). Plating efficiencies may be measured by counting the number of cells from the first image in the series and taking the ratio of colonies detected. Average plating efficiencies may be computed across identically dosed wells.

As an illustrative example experiment, the process may involve imaging 384 wells for 170 hours at 3 hour intervals which generates an enormous amount of data to be processed. Data from an individual plate may be composed of images sets that are 30 GB in size, for example. The processing technique pulls out features of the images which are processed to count cells and identify colonies. Images may be saved in RGB color images in 8 bit, with a resolution of 3 $\mu$m/pixel for further analysis by way of illustrative example. A 3×3 Gaussian filter, followed by a 5×5 median and rolling ball filter of radius 5 pixels may be applied to remove the noise from the images. A threshold may be set to convert the image to binary before applying a circle Hough transform to identify and count cells in some example embodiments.

For an illustrative example experiment, the binary images may be scaled, breaking a pixel into 16, to improve the detection rate of the circle Hough transform. Binary images may be dilated to create a mask to group cells. All cells were dilated to a disk of 30 $\mu$m radius (corresponding to 12 pixels on images collected with the 4× objective). All dilated objects whose boundaries overlap may be identified as a unique group and assigned a numeric identifier. The numeric identifiers provide labels using the connected components to have a unique numeric identifier from 1 to N, where N is the number of unique objects found in the image. The cell centroids may be mapped to the new image to identify the group to which they belong and a label connects components, for example.

The colony labels may be verified for consistent labelling through the time-lapse series. It is assumed that colonies grow such that their population centre, or centroid, remains within a localized neighborhood. To verify that the labels are consistent across images, the colony centroid from image $t_i$ may be projected to image $t_{i-1}$ to measure the Euclidean distance with all other colony centroids. The projected centroid may also be assigned the label of the nearest centroid. A bounding box that is the smallest possible rectangle may be drawn around the dilated group of cells and mapped to the first image $t_0$. If a bounding box contains more than 1 unique point from the first image, the group is claimed to not originate from a single cell and is not scored as a colony, thus confirming colonies to be clonogenic.

The process generates output data, at 410 (FIG. 4), for storage and further processing, such as a colony growth model to track colony forming behaviour over time, in response to therapy, and so on.

The colony population data may be analyzed to find characteristics of cell response to radiation. Colonies may be identified when groups of cells achieve a minimum population of 50. Colony growth characteristics may include established colony time, first doubling event, second doubling event, and so on. Colony growth data provide ability for a multiplicity correction. The expected number of colonies observed following an environmental perturbation is dependent probability of a single cell to survive the change of state. Colonies seeded by greater than 1 cell have an increased likelihood of forming a colony. These colonies can be identified and corrected to measure the true probability of survival. For example, if a colony is seeded with two cells A and B, the colony will survive if A survives, if B survives, or if both survive. In this case, the likelihood of an individual cell surviving can be treated as a binomial problem and can be calculated using known methods for solving binomial statistics.

For an illustrative experiment, the process may be applied to the image set from the 384 well microplate. The process may produce a survival fraction curve which may be fit with a linear-quadratic model. The parameters of this model (alpha-beta ALPHA±A–Beta±B) may be similar to $\alpha=0.499\pm0.021$ $Gy^{-1}=0.067\pm0.002$ $Gy^{-2}$. The high throughput assay may produce accurate results with the additional benefit of being able to measure time-dependent parameters which are unavailable to the standard assay. Colony growth can be observed through time and modelled to measure any radiation-induced changes to the growth rate. Increased observation from embodiments described herein may improve assay monitoring to detect colonies that may become confluent before the completion of a standard assay. The ability to differentiate neighbouring colonies has further decreased uncertainty of the absolute clonogenic colony population counts. The colony growth analysis may not be available to the standard clonogenic assay as the data is fixed to a single point in time. The increased temporal resolution available to the high throughput technique may have additional benefits over the standard assay as such an improved measurement characterizing cell growth and proliferation in response to drug-radiation therapy is now possible.

The process counting validation or verification may be performed using three wells and their image sets, chosen at random, using four parameters: total individual cell count, dead cell discrimination, cell grouping for colony identification. Manual counts may be performed on the three image sets recording the four parameters. The results may include total cell population counts. The total population growth curves and goodness of fit may verify accuracy of process as compared to manual counting methods, for example. The ruleset of the automated counting process may produce the same cell count for an image after every implementation whereas manual counting methods will exhibit random variations for the same image. The automated counting process may, therefore, be more precise than manual counting methods while achieving similar (or better) accuracy. The counting process of embodiments described herein may provide a more reliable cell and colony count using a more rigorous rule set for differentiating live and dead cells in comparison to manual counting.

The dosimetry of the micro well plate may indicate the therapy to be of high precision. For example, radiation may be delivered to 48 control points on the well microplate in 55 minutes with high precision. The dose flatness and symmetry may be analyzed. The flatness and symmetry measurements may indicate the collimated field to have negligible overlap between neighbouring control points. The confirmation of cell targeting and field symmetry may involve using the X-RAD™ cabinet irradiator for targeted therapy of cell in vitro assays. The X-RAD™ is held to clinical standards for dose rate calibration. While not an absolute dosimeter, the radiochromic film has confirmed the accurate targeting of wells and, by extension, the cells. The radiochromic film analysis has provided additional confirmation of the calibrated dose rates for the X-RAD™ irradiator.

Embodiments described herein may provide a reduction of labour and consumables, reduction in error from cell density estimation and the ability to perform time course analysis in comparison to simple end point measurement, for example.

For an example experiment, the entire high throughput clonogenic assay was completed in 9 consecutive days, the equivalent of an 85% decrease in labour time and 80% decrease in experimental turnaround in comparison to the standard assay. An estimation of cell suspension density may still be required as in the standard clonogenic assay; however, the error associated with the estimation is reduced by the ability to take an absolute measurement of cells plated using the image analysis algorithm. The high throughput clonogenic assay may measure the absolute number of cells seeded into a sample and has allowed increased sample monitoring throughout the experiment. The high throughput plating efficiency measurement may be better represented, as the absolute cell count is known at the cell seeding time point. A discrete end point is chosen to complete the experiment in the standard clonogenic assay, halting cell growth through fixing to measure the plating efficiency of a sample. The high throughput method has the ability to monitor cell growth and determine an endpoint based on cell confluency across the well microplate; image sets can be investigated at different time periods in the series based on how cells grow within a sample, thus increasing sample efficiency. The additional parameters available for measurement through time series analysis will allow an expanded and more accurate characterization of a cell's survivability and behavior with regard to therapy. Time-dependent parameters available to the high throughput assay may include colony growth dynamics, and cell proliferation. Transitioning the assay to a high throughput and miniaturized platform may decrease the amount of labour while increasing the viability of the results.

Embodiments described herein relate to a clonogenic assay optimized to be completed on an automated platform. Such a platform may incorporate the high throughput characteristics to achieve rapid data acquisition and processing.

The workflow for high throughput clonogenics can require less manual labour than the traditional clonogenic assay. The traditional clonogenic assay requires significantly more time to complete the assay than the high throughput method. The process enables updates for the ability to dynamically generate new experiment plans.

Figure 12:
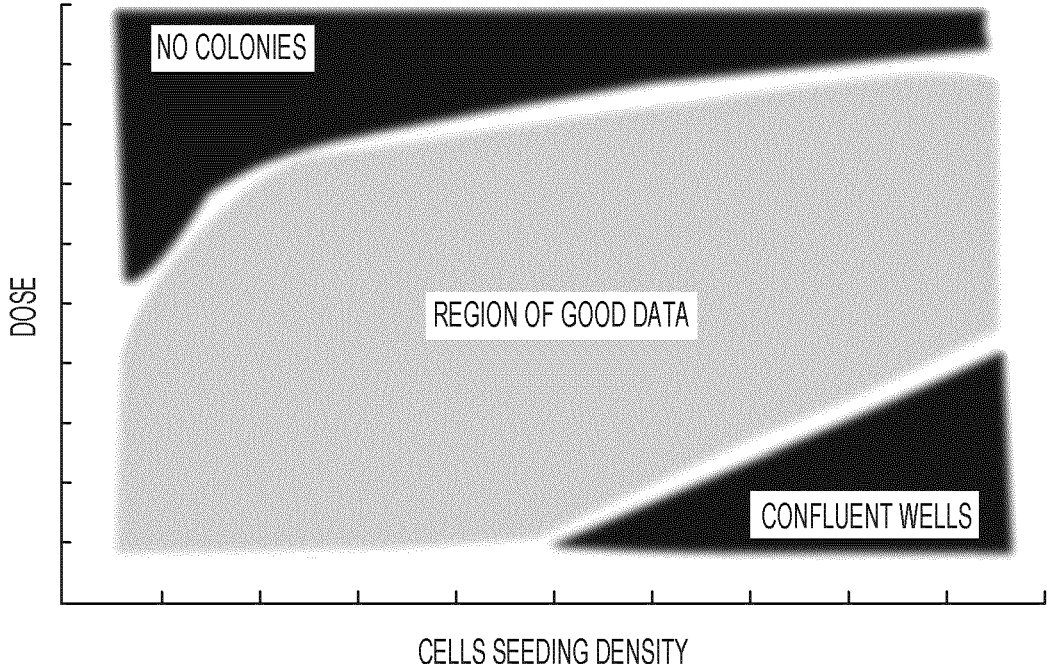
FIG. 12 is an example demonstration of the optimal dose and density region for produce good data.

FIG. 12 is an example demonstration of the optimal dose and density region for producing good data. The graph plots dose against cell seedling density. The graph shows a region of good data between regions with no colonies in a region with confluent wells. The graph can provide a description of the expected response of cells to a therapeutic dose. In regions of low cell density, a therapeutic dose may be extremely toxic such that no colonies are observed and are not producing clonogenic data. Similarly, the region where cell density is too great and colony formation is prolific will not produce easily identifiable single colonies for assaying.

Figure 13:
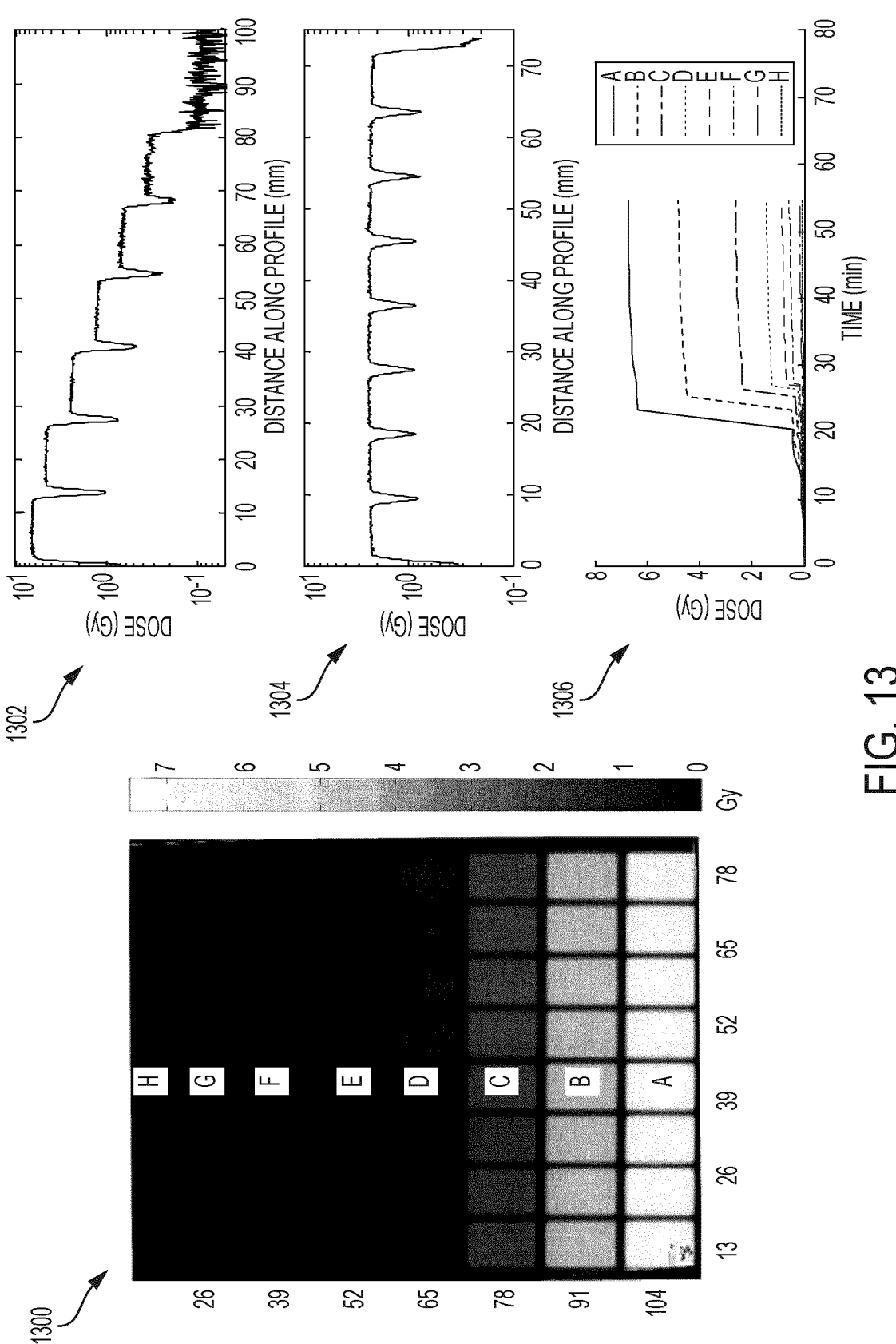
FIG. 13 is an example of improved dosimetry graph.

FIG. 13 is an example of micro well plate dosimetry. Graph 1300 is an image resulting from converting optical opacity to dose following the exposure of radiochromic EBT2 film. Additional graphs 1302, 1304, are dose line profile of the radiochromic film. A single radiation point has a specific profile that can be characterised. The profile can be used to model the out of field dose being deposited with each radiation point. Plot 1306 show the mean dose contribution of each radiation point within an ROI over time.

Figure 14:
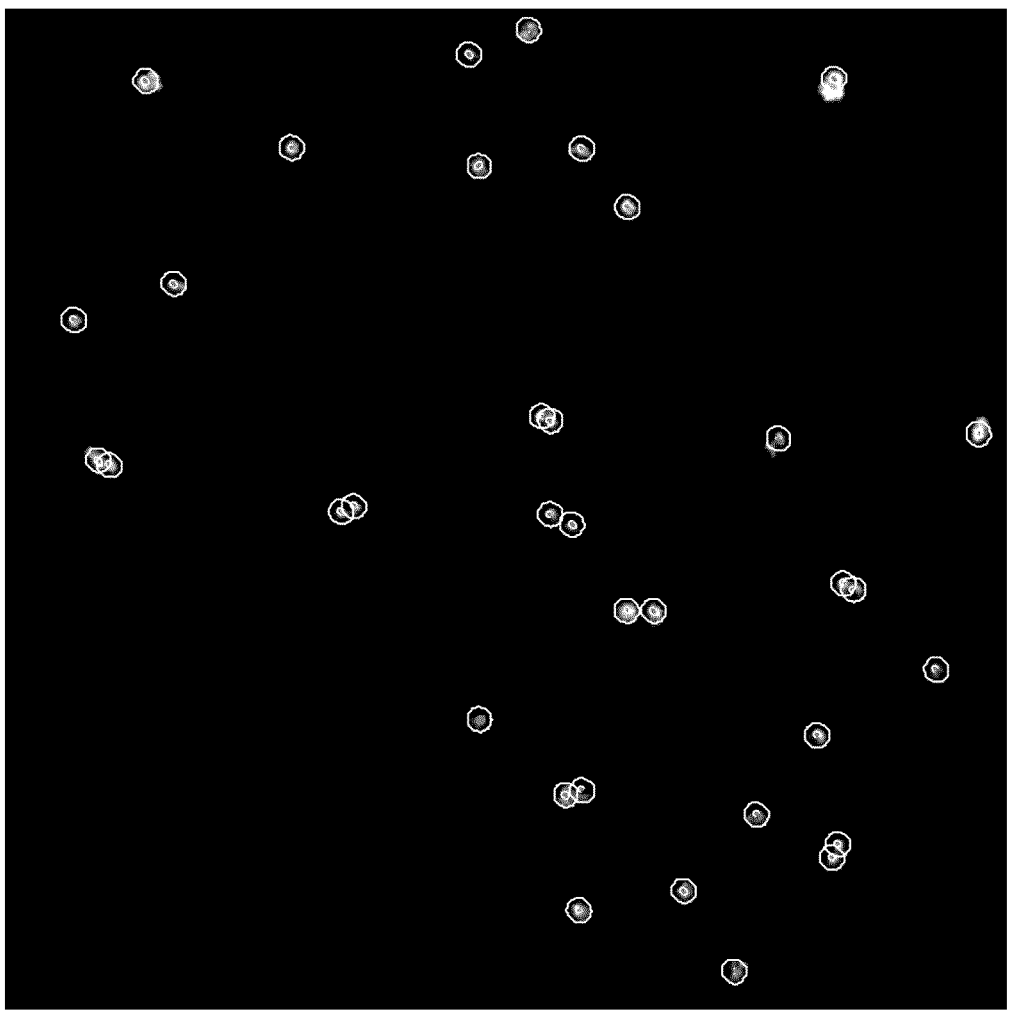
FIG. 14 is an example image identifying cell centroids and the cell grouping metric.

FIG. 14 is an example image identifying cell centroids and the cell grouping metric. Cell centroids are identified as points within the cells. Each cell is checked for its proximity with its neighbor and grouped following the minimum separation criterion as demonstrated by the circles surrounding the cells.

Figures 15A, 15B, 15C:
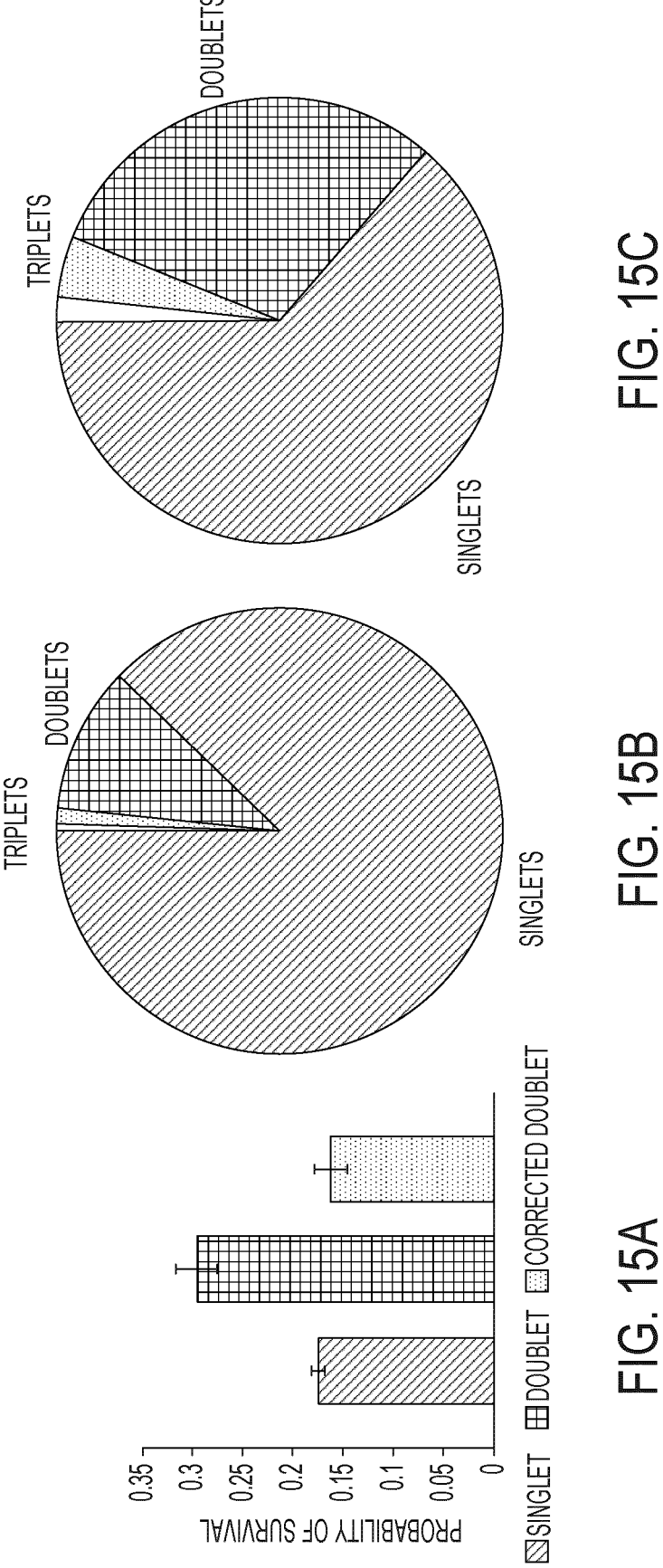
FIGS. 15A, 15B, 15C are example graphs for performing the cell multiplicity correction and the influence of time on the distribution of doublets and singlets.

FIGS. 15A, 15B, 15C are example graphs to provide an example of performing the cell multiplicity correction and the influence of time on the distribution of doublets and singlets. Colony growth histories may be analyzed from time course analysis to measure time based behaviour of the cells' exposure to a therapy protocol. The times groups become colonies may be binned into histograms to investigate dose dependent shifts in established colony times. Colony histories may be used to measure cell multiplicity distribution during the therapeutic protocol. FIG. 15A describes how cell multiplicity may bias the observed likelihood of survival. This bias may be modelled using the binomial distribution as described by Equation 1. An example of this modelling is considered for the case of n=1. One cell has the probability of forming a colony, the alternative outcome being the cell not forming a colony. The possible values of k are therefore 0 or 1. The likelihood of a single cell, n=1, of forming a colony, k=1 is $$P(1,1) = \binom{1}{1} p^1 (1-p)^{1-1} \qquad \text{[Equation 6]}$$

$$P(1,1) = p \qquad \text{[Equation 7]}$$

Therefore, the likelihood of a single cell forming a colony is the probability of the cell surviving the therapy. For cases when observing n cells, k={0, 1, 2 . . . , n−1,n}. It is not always possible to determine which cell is the base colony forming unit. Instead, the unit is described as the likelihood of forming at least one colony, P(n,k≠0), which may be described by $$P(n, k \neq 0) = 1 - P(n, k = 0) \qquad \text{[Equation 8]}$$

$$P(n, k \neq 0) = 1 - \binom{n}{0} p^0 (1 - p)^{n-0} \qquad \text{[Equation 9]}$$

$$P(n,k \neq 0) = 1 - (1-p)^n \qquad \text{[Equation 10]}$$

Recall that P(n, k≠0) is a measurable quantity described by Equation 2. Equation 10 may be rearranged to determine the probability of survival in terms of measurable quantities $$p = 1 - (1-P)^{1/n} \qquad \text{[Equation 11]}$$

FIG. 15A illustrates the likelihood of a doublet forming a colony being greater than the likelihood a singlet; however, once corrected, it is shown that each cell has the same probability of survival. FIG. 15B illustrates experiments with distributions of singlet, doublet, and triplet cell populations when seeded. FIG. 15C refers to experiments requiring latency between seeding and therapy administration. The duration of this latency will have an effect on the distribution of cell multiplicity. Since doublets and n-lets may influence the outcome of an experiment it becomes paramount to know the distribution of cell multiplicity at the time therapy is administered as to correct the bias that multiplicity introduces. By observing the multiplicity a correction can be performed to measure the true probability of survival. Each cell has the potential to divide and grow to produce progeny. The graph and output data for dynamic cell proliferation and viability and growth delay may plot mean with standard error of the mean in error bars.

Figure 16A:
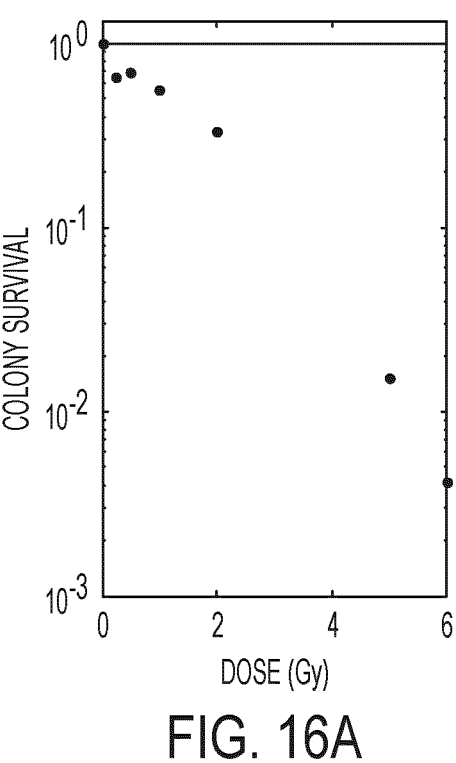
FIGS. 16A, 16B, 16C, 16D are example graphs for identifying models to fit to cell survival curves.
Figure 16B:
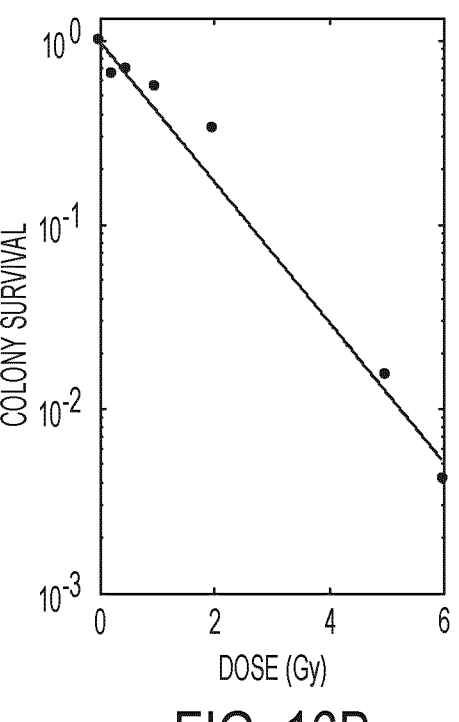
Figure 16C:
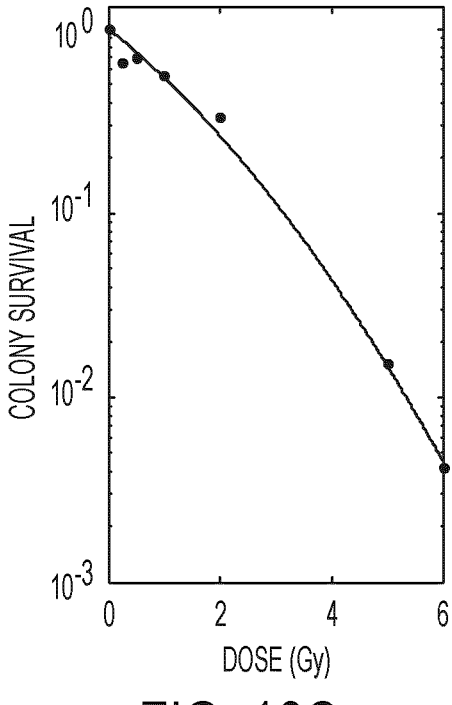
Figure 16D:
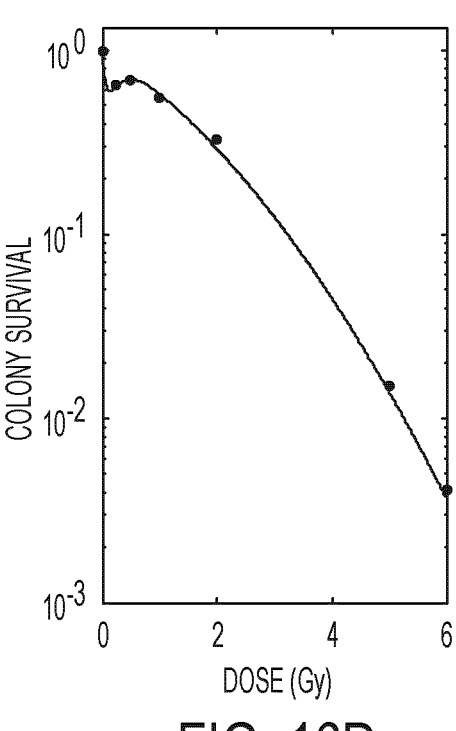

FIGS. 16A, 16B, 16C, 16D are example graphs for identifying models to fit to cell survival curves. At 618 (FIG. 6), the device 100 may determine whether the model is sufficient by comparing dose points to a curve for the model. The curve should intersect with most of the dose points, such as graph D, for example. There may be outlier points that do not map to the curve even though the model is sufficient. Examples of models applied to fit theoretical data are shown in the graphs of FIGS. 16A, 16B, 16C, 16D. In FIG. 16A the data is modelled with a constant. In this example model is incorrect. In FIG. 16B the data is modelled with a linear exponential decrease in survival. The model demonstrates that there is an effect, however, there is significant deviation from the data points. In FIG. 16C the data is modelled using the linear quadratic model for cell survival. Alternative models may be considered to further improvement to fit to account for deviation from the models. FIG. 16D shows an induced repair model. The resolution of the data may be too poor to effectively model and interrogate this region of the effect. If further poor models are generated, further data points are required to populate regions of poor resolution.

Figure 17:
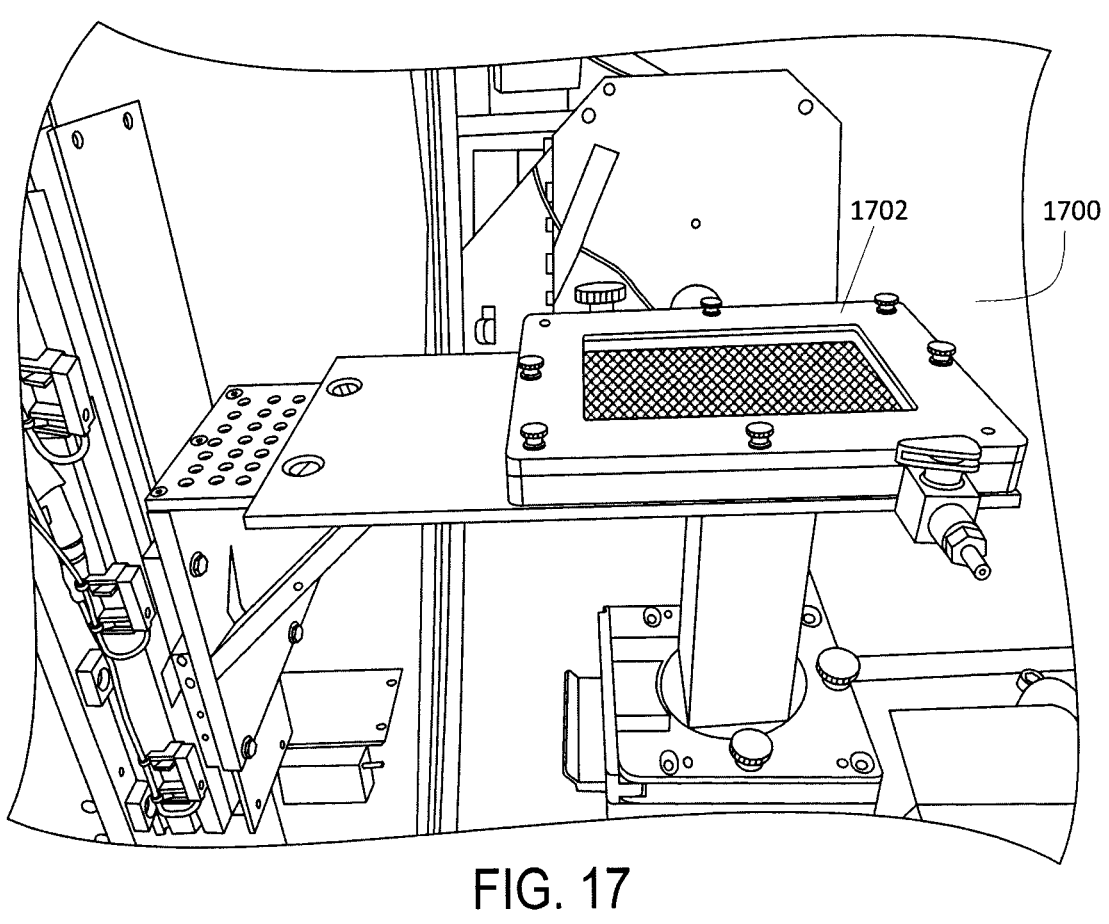
FIG. 17 illustrates an example irradiation system.

FIG. 17 illustrates an example irradiation system 1700 with a microchamber 1702.

Figure 18:
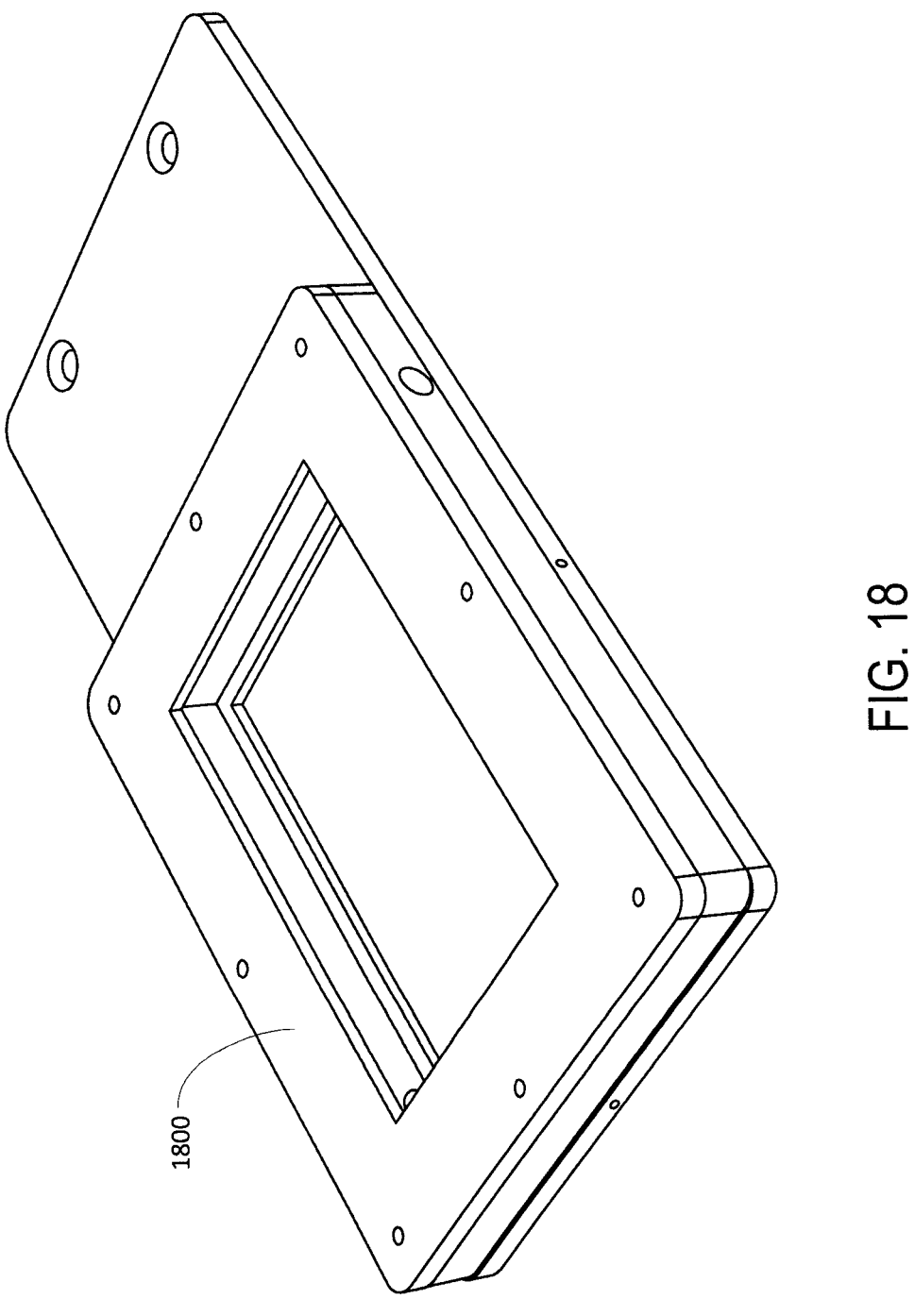
FIG. 18 illustrates an example irradiation system.

FIG. 18 illustrates an example of an environmental microchamber 1800 used to maintain an environmental condition, such as hypoxia, during a radiation delivery protocol.

Figure 19:
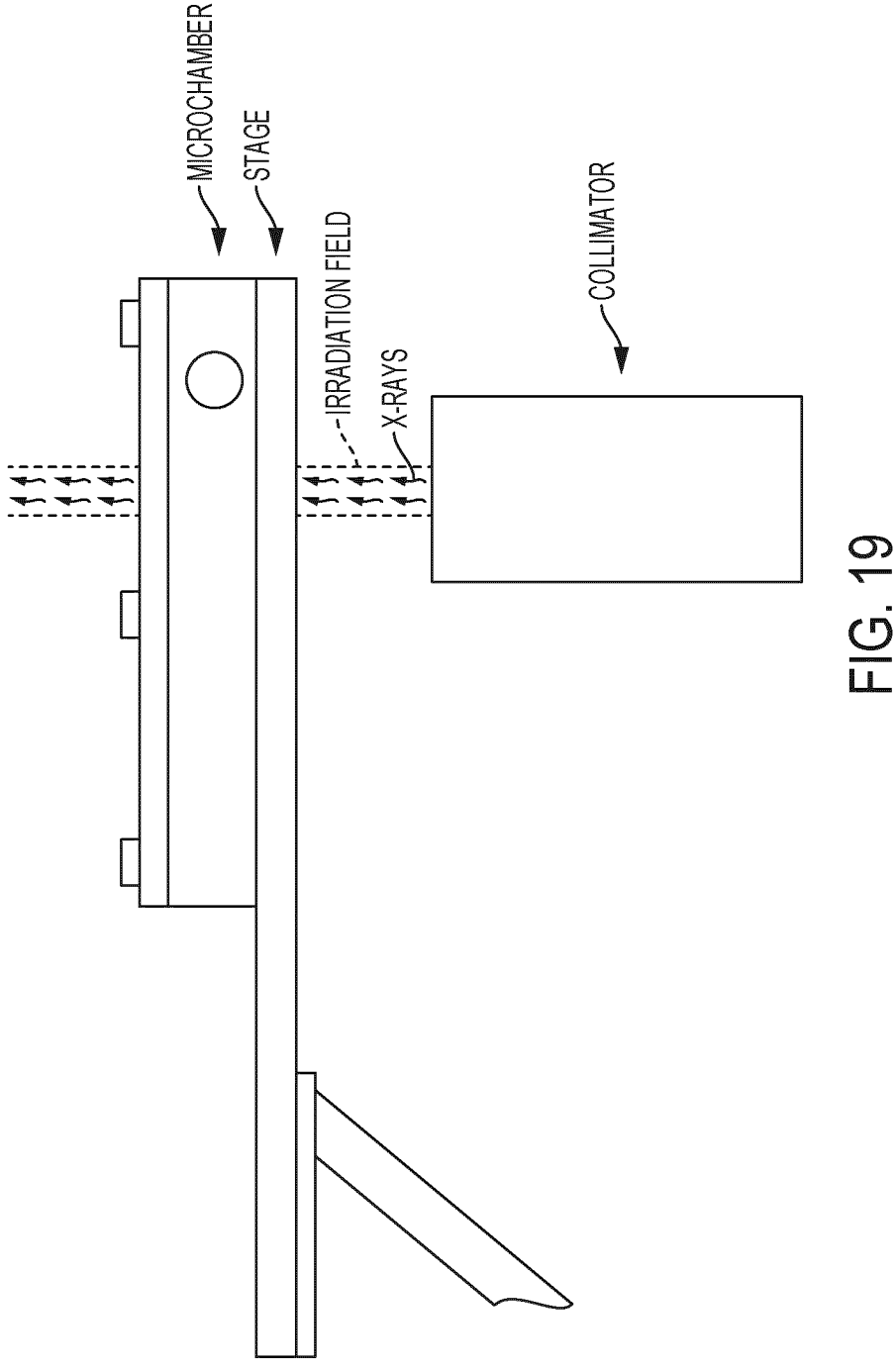
FIGS. 19 and 20 illustrate an example setup with well plate, stage, and irradiator.

FIG. 19 illustrates an example setup with well plate, stage, and irradiator. The well plate may be mounted on a moving stage which will allow individual wells to be moved in and out of the radiation field to provide the dose prescribed by a therapeutic protocol. A collimator can attenuate the x-rays to modify the radiation field to ensure proper administration of dose to a particular well or group of wells, and to limit dose to neighboring wells.

Figure 20:
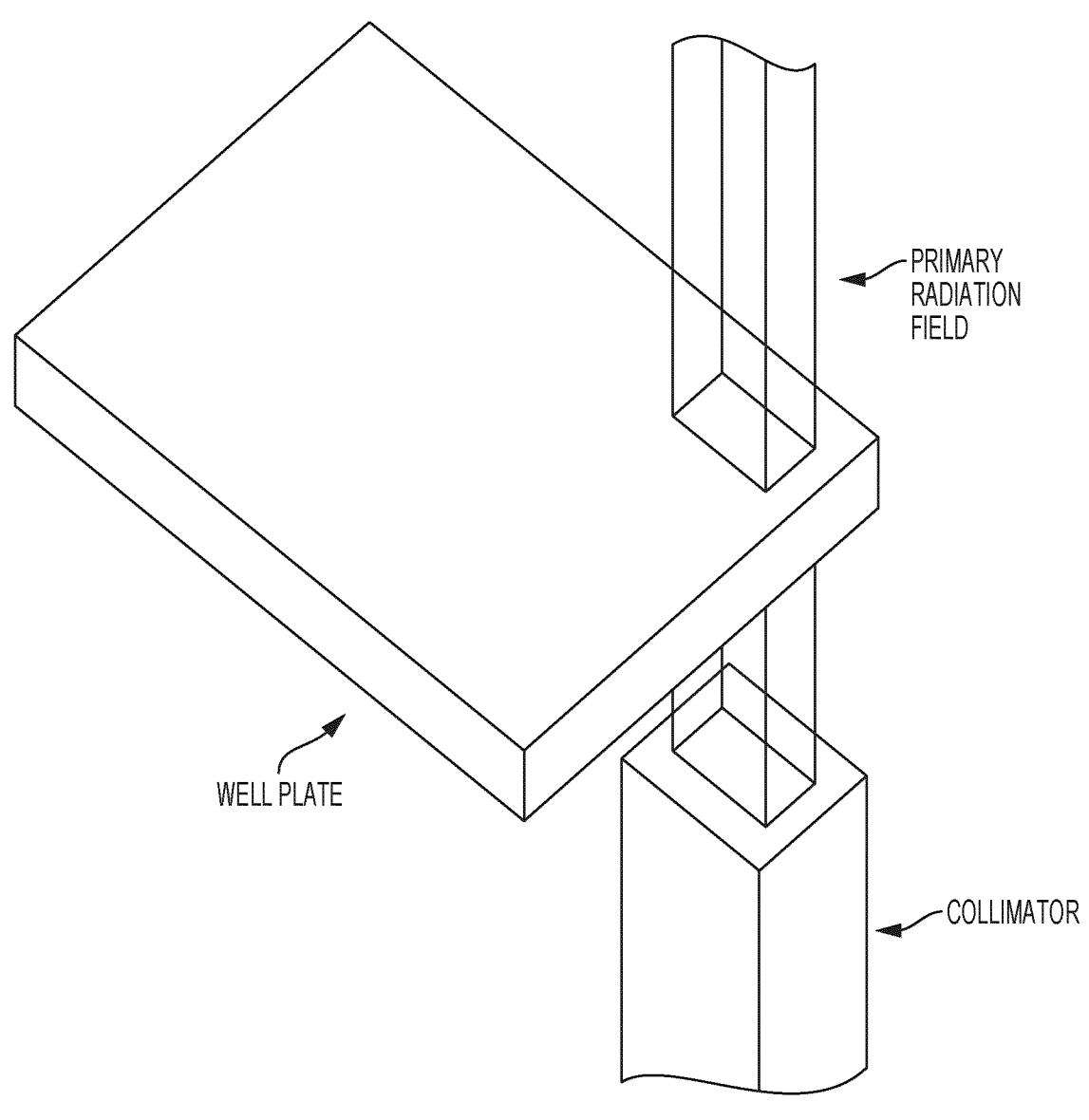

FIG. 20 is another view of FIG. 19.

Embodiments described herein process temporal images for an automated clonogenic assays for tissue cells (particularly tumour cells) to allow for monitoring of effects of therapy on survival and proliferation. Embodiments described herein may integrate with radiation therapy device, such as an x-ray irradiation device to allow integration of the radiation and the processing and monitoring of the cell growth and sensitivity of the cell growth to the therapy. The process combined with ongoing image monitoring looks at tracking the cell colony behavior and particularly mapping distance from original cell as the colony grows to help determine an accurate quantification of colony numbers (for example to allow accurate counting when colonies merge during an experiment and become indistinguishable when one tries to count them at the end of the experiment without tracking them throughout the experiment). Cells are imaged on the basis of fluorescence arising from an in vivo cell reporter introduced that produces fluorescence, for example. The monitoring of tissue cells may be used to compute sensitivity to therapy for the clonogenic assays using fixation and staining.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The foregoing discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

For simplicity only one device 100 is shown but system may include more devices 100, which may be the same or different types of devices 100. The device 100 has at least one processor, a data storage device 210 (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing"). Device 100 includes at least one processor, memory, at least one I/O interface, and at least one network interface.

Each processor may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. Memory may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface enables device 100 to interconnect with one or more input devices, such as a keyboard, mouse, camera, touch screen and a microphone, or with one or more output devices such as a display screen and a speaker.

Each network interface enables device 100 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Device 100 is operable to register and authenticate users (using a login, unique identifier, and password for example) prior to providing access to applications, a local network, network resources, other networks and network security devices.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A high throughput radiobiology assay platform for plating cell cultures and triggering cell therapy using computed treatment protocols, the platform comprising:

a hardware processor having a communication interface to an imaging system for continuously receiving temporal images of growth of cells at intervals over a time period before and after a therapy, wherein the hardware processor connects to a cell loading device that loads various concentrations of the cells based on a therapeutic protocol for cell density and therapy delivery, the therapeutic protocol comprising a pattern of cell seeding and therapy doses for delivery to said cells, wherein the hardware processor connects to a therapy system for delivering the therapy by application of different doses to different cells or groups of said cells based on the therapeutic protocol for the cell density and the therapy delivery, wherein the hardware processor couples the therapy system to a radiation delivery device for delivering radiation therapy to said cells as part of the therapy;

a non-transitory memory for storing data structures for the images and colony formation behavior of individual cells in the images;

wherein the hardware processor is configured to automatically process the temporal images to detect relations between individual cells in the images to track the colony formation behavior of the individual cells in the images from said growth of the cells at the intervals over the time period and compute a likelihood of survival of the individual cells after the therapy to a specific dose as the temporal images are received over the time period, wherein the hardware processor identifies and classifies the individual cells and colonies based on their initial multiplicity, wherein the hardware processor is configured to automatically process the temporal images by:

filtering or removing background from the temporal images;

detecting or locating cell centroids in the filtered temporal images;

grouping the cell centroids and corresponding cells based on a distance criterion between the cell centroids to find and detect group centroids; and writing output data for generating the therapeutic protocol to the non-transitory memory by updating the data structures in the non-transitory memory with group identifiers, the group centroids, and a group population; and the hardware processor is configured to generate the therapeutic protocol, wherein the hardware processor is configured to trigger loading of said cells and delivery of the therapy to said cells based on the therapeutic protocol, wherein the hardware processor generates the therapeutic protocol to configure and control the cell loading device for loading said cells and the therapy system for delivering therapy, wherein the hardware processor triggers the therapy system and the radiation delivery device to execute the therapeutic protocol to deliver radiation therapy and/or drug therapy in a controlled microenvironment;

wherein the hardware processor continuously monitors the temporal images of the growth of the cells at the intervals over the time period before and after the therapy, wherein the hardware processor is configured to process the temporal images generated after delivery of the therapy to measure sensitivity of said cells to the therapy and/or the radiation therapy using fixation and staining, wherein the hardware processor stores the measured sensitivity to the therapy and/or the radiation therapy in the data structures of the non-transitory memory;

wherein the hardware processor refines and updates the therapeutic protocol based on the measured sensitivity to the therapy and/or the radiation therapy stored in the data structures of the non-transitory memory;

wherein the hardware processor is configured to process the data structures stored in the non-transitory memory to update or develop the therapeutic protocol for the cell density and the therapy delivery, wherein the hardware processor computes the therapeutic protocol based on the colony formation behavior, a model of cell survival from the likelihood of survival of the individual cells, and a number of cells required for observation by the hardware processor using the temporal images to compute the therapeutic protocol with the pattern of the cell seeding plan and the therapy doses to achieve acceptable statistical uncertainty within a statistical target for the model of cell survival.

2. The platform of claim 1, further comprising a sealable chamber that can maintain a low oxygen environment for testing the therapy in the controlled microenvironment for a variety of environmental oxygen conditions.

3. The platform of claim 2, the hardware processor for further processing the temporal images of colony formation to measure sensitivity of said cells to both the therapy and a radiation therapy, the non-transitory memory for storing, in the data structures, the measured sensitivity to both the therapy and the radiation therapy.

4. The platform of claim 1, wherein the hardware processor is configured for triggering the therapy system for delivery of the therapy as an initial therapy and an additional therapy based on the measured sensitivity of said cells to the therapy.

5. The platform of claim 1, wherein the cells are in wells of a multi-well plate, the platform further comprising the imaging system, for generating the temporal images of the colonies, the imaging system comprising a microscope that generates serial images of said cells in the multi-well plate at the intervals over the time period before and after delivery of the therapy to generate at least a portion of the temporal images, wherein the communication interface of the hardware processor couples to the microscope to receive the images from the microscope.

6. The platform of claim 1, wherein the therapeutic protocol defines a group of cells as a colony using a classifier derived from information about both a number of cells in a certain region of interest and the spatio-temporal history of the cells involved.

7. The platform of claim 1, further comprising a robotic cell loading device that automatically loads the cells into a multi-well plate and different concentrations of said cells into different wells of the multi-well plate, wherein the hardware processor connects to the robotic cell loading device directly or via a network connection to interact with the robotic cell loading device to differentially load said cells to match an anticipated dose and survival probability for the therapy.

8. The platform of claim 7, wherein the therapy system comprises an irradiator, wherein the therapeutic protocol further comprises a pattern of optimized radiation doses for delivery by the irradiator to the different wells of the multi-well plate, wherein the hardware processor is configured to compute the optimized radiation doses based on cell survival and statistical uncertainty.

9. The platform of claim 1, wherein the cells are in wells of a multi-well plate, wherein the hardware processor to extract cell locations in the multi-well plate from the temporal images, detect cell centroids as points within the cells in the temporal images, and automatically identify colonies of the cells in the temporal images using the cell centroids to track the colony formation behavior.

10. The platform of claim 5, wherein the imaging system comprises a fluorescent microscope, wherein at least a portion of the temporal images are fluorescent images, wherein at least a portion of the cells comprise a fluorescent in vivo cell reporter to measure said growth of the cells.

11. The platform of claim 7, further comprising the therapy system that applies different therapy doses to the different wells of the multi-well plate, wherein the hardware processor triggers the therapy system for application of the different therapy doses to the different wells of the multi-well plate.

12. The platform of claim 11, wherein the therapy system comprises an irradiation system that delivers the therapy in the form of x-rays, electrons, gamma-rays, or hadrons, or other sources and forms of radiation, wherein the different therapy doses are based on different therapy rates delivered to each well or different x-ray energies delivered to each well.

13. The platform of claim 1, wherein the therapeutic protocol further comprises patterns of drug dose delivery, patterns of radiation dose delivery, or patterns of environmental factors comprising oxygen and heat.

14. The platform of claim 1, wherein the hardware processor receives or captures data on changes in the growth of the cells after a treatment based on image analysis of growth rate of the cells and cell cycle position in the temporal images.

15. The platform of claim 7, wherein the hardware processor generates an optimized seeding protocol using recursive cell plating optimization that assigns cells to wells and therapy doses to the wells by determining the number of cells required for observation to achieve the acceptable statistical uncertainty within the statistical target for the model of cell survival, and triggers cell seeding by the robotic cell loading device using the seeding protocol.

16. The platform of claim 1 wherein the cells are in wells of a multi-well plate, wherein the therapeutic protocol indicates different therapy doses to different wells, the platform further comprising the therapy system that applies the different therapy doses to the different wells of the multi-well plate, wherein the therapy system comprises a hardware processor to execute instructions for the therapeutic protocol, wherein the therapy system delivers at least one of radiation therapy and drug therapy, wherein the therapeutic protocol comprises at least one of a pattern of radiation doses and a pattern of drug dose delivery.

17. The platform of claim 1 wherein the hardware processor is configured to define a group of cells as a colony using a classifier derived from information extracted from the temporal images about both a number of cells in a region of interest and spatio-temporal history of the cells.

18. The platform of claim 1 wherein the hardware processor tracks the colony formation behavior by removing background noise from the images, detecting one or more cell centroids in the images, each cell centroid being a unit of a group of cells that satisfy a minimum spatial separate criteria, and, for each detected cell centroid, grouping the respective group of cells into a colony if the group of cells for the respective detected cell centroid meets or exceeds a threshold number of cells, wherein the hardware processor issues write comments to the non-transitory memory to update the data structures with group identifiers, the group centroids, and group population.

19. The platform of claim 1 wherein the hardware processor is configured to track the colony formation behavior in the temporal images by extracting cell locations from the temporal images and automatically identifying, characterizing, and localizing colonies of cells in the temporal images.

20. The platform of claim 1 wherein the cells are in wells of a multi-well plate, wherein the hardware processor is configured to, for each well, for each image associated with the respective well, remove or filter background noise from the image; find cell centroids in the filtered images; grouping the cell centroids; and writing output data for dynamic cell proliferation and viability and growth delay to the non-transitory memory.

21. The platform of claim 1, wherein the cell loading device further comprises a non-transitory memory and a hardware processor to execute program instructions stored therein to program the cell loading device for automatically loading different concentrations of cells, the cell loading device configured by the program instructions to load a well plate of the cells to match an anticipated dose and survival probability for a treatment, wherein the temporal images are of the cells growing in the well plate.

22. The platform of claim 21 wherein the hardware processor is configured to identify regions in the image of poor data resolution, add additional dose points to the model of cell survival, and generate a seeding protocol for cell seeding by the cell loading device that assigns cells to wells of the well plate and the therapeutic protocol of a pattern of therapeutic doses to the wells of the well plate to achieve the statistical target to improve colony detection.

23. The platform of claim 1, wherein a high throughput radiobiology assay is a two-dimensional assay, and wherein the temporal images comprise two-dimensional images.

24. The platform of claim 1, further comprising the therapy system for the delivery of the therapy to said cells based on the therapeutic protocol, wherein the therapy system comprises an irradiator, wherein the cells are in wells of a multi-well plate, wherein the irradiator applies different radiation doses to different wells of the multi-well plate according to the therapeutic protocol.

25. The platform of claim 1, wherein the hardware processor receives, as an input, different therapeutic parameters comprising drug type, dose parameters, radiation dose rate, and environmental conditions and generates or updates the therapeutic protocol using the different therapeutic parameters.

26. The platform of claim 1, further comprising a client device having an interface to display visual elements relating to the therapeutic protocol, a survival curve generated based on the temporal images, the temporal images, portions of the model of cell survival, wherein the hardware processor controls components of the interface, receives commands at the interface, and generates the visual elements representing the survival curve and the therapeutic protocol at the interface.

* * * * *